US008529872B2

(12) United States Patent
Frank et al.

(10) Patent No.: US 8,529,872 B2
(45) Date of Patent: Sep. 10, 2013

(54) SEEDS AND MARKERS FOR USE IN IMAGING

(75) Inventors: Steven J. Frank, Bellaire, TX (US); Karen Martirosyan, Houston, TX (US)

(73) Assignees: Board of Regents, The University of Texas System, Austin, TX (US); The University of Houston System, Houston, TX (US)

( * ) Notice: Subject to any disclaimer, the term of this patent is extended or adjusted under 35 U.S.C. 154(b) by 555 days.

(21) Appl. No.: 12/668,585

(22) PCT Filed: Jul. 11, 2008

(86) PCT No.: PCT/US2008/069861
§ 371 (c)(1),
(2), (4) Date: Jun. 4, 2010

(87) PCT Pub. No.: WO2009/009760
PCT Pub. Date: Jan. 15, 2009

(65) Prior Publication Data
US 2010/0254897 A1 Oct. 7, 2010

Related U.S. Application Data

(60) Provisional application No. 60/949,157, filed on Jul. 11, 2007.

(51) Int. Cl.
*A61K 51/00* (2006.01)
*A61M 36/14* (2006.01)

(52) U.S. Cl.
CPC ..................................... *A61K 51/00* (2013.01)
USPC ........................................ 424/1.11; 424/1.89

(58) Field of Classification Search
USPC ........................................................ 424/1.29
See application file for complete search history.

(56) References Cited

U.S. PATENT DOCUMENTS

| | | | | |
|---|---|---|---|---|
| 4,167,564 | A * | 9/1979 | Jensen | 514/1.2 |
| 5,628,982 | A | 5/1997 | Lauffer et al. | |
| 5,713,828 | A * | 2/1998 | Coniglione | 600/7 |
| 6,333,971 | B2 | 12/2001 | McCrory et al. | |
| 6,521,773 | B1 | 2/2003 | Hainfeld | |
| 6,534,039 | B2 | 3/2003 | Hainfeld | |
| 6,575,888 | B2 * | 6/2003 | Zamora et al. | 600/3 |
| 7,418,289 | B2 | 8/2008 | Hyde et al. | |
| 2002/0028993 | A1 | 3/2002 | Hainfeld | |
| 2003/0228255 | A1 | 12/2003 | Park et al. | |
| 2004/0109823 | A1 | 6/2004 | Kaplan | |
| 2004/0225231 | A1 | 11/2004 | Ehr | |
| 2005/0107870 | A1 | 5/2005 | Wang et al. | |
| 2007/0218009 | A1 * | 9/2007 | van Veggel et al. | 424/9.34 |
| 2011/0118532 | A1 * | 5/2011 | Kaplan | 600/8 |

FOREIGN PATENT DOCUMENTS

| | | |
|---|---|---|
| WO | 0038738 | 7/2000 |
| WO | 0207846 | 1/2002 |
| WO | 2009009760 | 1/2009 |

OTHER PUBLICATIONS

Rohrer et al. (Invest. Radiol. 2005, 40, 715-724).*
Paramagnetism Wikipedia 2013.*
Fuller, C.D., et al., "Fiducial Markers in Image-guided Radiotherapy of the Prostate", Reference Section, US Oncological Disease 2006, [retrieved from the Internet on Jun. 18, 2012 using <URL: http://www.touchbriefings.com/pdf/2460/ACF201.pdf>].
Lee, R., et al., "A Magnetic Resonance-based Seed Localization Method for I-125 Prostate Implants", Journal of Korean Medical Science 2007, vol. 22, pp. S129-S133, copyright The Korean Academy of Medical Sciences.
Brigham and Women's Hospital, "Prostate Cancer Radiation Oncology Service", [retrieved from the Internet on Mar. 3, 2008 using <URL: http://www.brighamandwomens.org/patient/prostatecancer-radiation.aspx>].
Susil, R., et al., "System for MR Image-guided Prostate Interventions: Canine Study", Radiology, Sep. 2003, vol. 228, No. 3, pp. 886-894.
Schueler, B., et al., "MRI Compatibility and Visibility Assessment of Implantable Medical Devices", Journal of Magnetic Resonance Imaging, vol. 9, pp. 596-603, copyright 1999 Wiley-Liss, Inc.
Giebeler, A., et al., "Dose perturbations from implanted helical gold markers in proton therapy of prostate cancer", Journal of Applied Clinical Medical Physics, vol. 10, No. 1, Winter 2009.
Kry, S., et al., "Investigation into the use of a MOSFET dosimeter as an implantable fiducial marker", Journal of Applied Clinical Medical Physics, vol. 10, No. 1, Winter 2009, [retrieved from the Internet on Mar. 3, 2009 using <URL: http://www.jacmp.org/index.php/jacmp/rt/printerFriendly/2893/1515>].
Patel, D., et al., Poly(D, L-lactide-co-flycolide) coated superparamagnetic iron oxide nanoparticles: Synthesis, characterization and in vivo study as MRI contrast agent; Colloids and Surfaces A: Physicochem. Eng. Aspects; 313-314 (2008) 91-94.
Young, L., International Search Report for International Patent Application No. PCT/US08/69861, dated Sep. 26, 2008.
Young, L., Written Opinion for International Patent Application No. PCT/US08/69861, dated Sep. 26, 2008.
Kupelian, P., et al., "Prostate Cancer: Image Guidance and Adaptive Therapy", Abstract, Advances in the Treatment Planning and Delivery of Radiotherapy, copyright 2007 S. Karger AG, Basel, vol. 40, pp. 289.
"Visicoil—Linear Fiducial Marker", Core Oncology, copyright Jan. 2008.
Sam Nordic, "Seeds", [retrieved from the Internet on Jun. 18, 2010 using <URL: http://www.samedical.se/radioterapi/engradiomain.htm>].
Baharlou, S., International Preliminary Report on Patentability for International Patent Application No. PCT/US2008/069861, The International Bureau of WIPO, dated Jan. 12, 2010.

(Continued)

*Primary Examiner* — Michael G Hartley
*Assistant Examiner* — Melissa Perreira
(74) *Attorney, Agent, or Firm* — Locke Lord LLP

(57) ABSTRACT

A contrast marker having a casing and a novel MRI contrast agent comprising metal complexes disposed around, within, or abutting the casing is provided. Such contrast markers may be placed in a strand, with or without a therapy seed, to produce a seeded strand useful for imaging and in connection with brachytherapy.

17 Claims, 26 Drawing Sheets

(56) References Cited

OTHER PUBLICATIONS

Hubner, W., Annex to the Invitation to Pay Additional Fees—Communication Relating to the Results of the Partial International Search for International Patent Application No. PCT/US2012/022092, European Patent Office, dated Apr. 11, 2012.

Frank, S., "A Toxicokinetic Evaluation of Intraprostatically Administered Cobalt Dichloride—N-Acetyl Cysteine (CoCl2-NAC) Conjugate in a Rat Model of Systemic Exposure", International Journal of Radiation Oncology Biology Physics, vol. 81, No. 2, pp. 2464, dated Oct. 2, 2011, abstract.

Clegg, W., Lacy, O.I., and Straughan, B., "Structures of Three Glycine-Bridged Polymeric Complexes: [Mn (glycine)(H2O)2Cl2], [Co(glycine)(H2O)2Cl2] and [Co(glycine)(H2o)4](NO3)2," Acta Crystallographica, 1987, Section C43, pp. 794-797, copyright 1987 International Union of Crystallography.

Stenzel, K. and Fleck, M., "Poly[[[diaquacobalt(II)]-di-µ-glycine] dichloride]," Metal-Organic Papers, Acta Crystallographica, Sep. 25, 2004, Structure Reports Online, Section E60, pp. m1470-1472, copyright 2004 International Union of Crystallography.

Frank, S.J., et al., "A Novel MRI Marker for Prostate Brachytherapy," Rapid Communication, accepted for publication Jan. 23, 2008, International Journal of Radiation Oncology Biology Physics, vol. 71, No. 1, pp. 5-8, copyright 2008 Elseveir Inc.

Nicolle, G.M., et al., "The Impact of Rigidity and Water Exchange on the Relaxivity of a Dendritic MRI Contrast Agent," Chemistry—A European Journal, 2002, vol. 8, No. 5, pp. 1040-1048, copyright 2002 Wiley-VCH.

Shastri, V.P., "Non-Degradable Biocompatible Polymers in Medicine: Past, Present and Future," Current Pharmaceutical Biotechnology, 2003, vol. 4, pp. 331-337, copyright 2003 Bentham Science Publishers Ltd.

Perez-Mayoral, E., et al., "Chemistry of paramagnetic and diamagnetic contrast agents for Magnetic Resonance Imaging and Spectroscopy pH responsive contrast agents," European Journal of Radiology, 2008, vol. 67, pp. 453-458, copyright 2008 Elsevier Ireland Ltd.

Sitharaman, B. and Wilson, L.J., "Gadonanotubes as new high-performance MRI contrast agents," International Journal of Nanomedicine 2006, vol. 1, No. 3, pp. 291-295, copyright 2006 Dove Medical Press Limited.

Donahue, K.M., Weisskoff, R.M., and Burstein, D., "Water Diffusion and Exchange as They Influence Contrast Enhancement," Journal of Magnetic Resonance Imaging, Jan./Feb. 1997, pp. 102-110, copyright 1997 ISMRM.

Toth, E., et al., "Water-Soluble Gadofullerenes: Toward High-Relaxivity, pH-Responsive MRI Contrast Agents," Journal of the American Chemical Society, vol. 127, No. 2, 2005, pp. 799-805, published Dec. 17, 2004, American Chemical Society.

Bloembergen, N. and Morgan, L.O., "Proton Relaxation Times in Paramagnetic Solutions. Effects of Spin Relaxation," The Journal of Chemical Physics, vol. 34, No. 3, pp. 842-850, Mar. 1961.

Crook, J., "Interobserver Variation in Postimplant Computed Tomography Contouring Affects Quality Assessment of Prostate Brachytherapy," Brachytherapy, 2002, vol. 1, No. 2, pp. 66-73, copyright 2002 Elseveir Inc.

Bloch, B.N. et al., "Prostate Cancer: Accurate Determination of Extracapsular Extension with High-Spatial-Resolution Dynamic Contrast-enhanced and T2-weighted MR Imaging—Initial Results", Radiology, Genitourinary Imaging, vol. 245, No. 1, pp. 176-185, Oct. 2007, copyright 2007 RSNA.

McLaughlin, P.W., et al., "Functional Anatomy of the Prostate: Implications for Treatment Planning," International Journal of Radiation Oncology Biology Physics, 2005, vol. 63, No. 2, pp. 479-491, copyright 2005 Elseveir Inc.

Lauffer, R.B., et al., "Hepatobiliary MR Contrast Agents: 5-Substituted Iron-EHPG Derivatives", Magnetic Resonance in Medicine, vol. 4, pp. 582-590, 1987, copyright 1987 Academic Press Inc.

Caravan, P., et al., "Gadolinium(III) Chelates as MRI Contrast Agents: Structure, Dynamics, and Applications", Chemical Reviews, vol. 99, pp. 2293-2352, 1999, copyright 1999 American Chemical Society.

Borel, A., Helm, L., and Merbach, A.E., "Molecular Dynamics Simulations of MRI-Relevant GdIII Chelates: Direct Access to Outer-Sphere Relaxivity", Chemistry—A European Journal, vol. 7, No. 3, pp. 600-610, 2001, copyright 2001 Wiley-VCH Verlag GmbH.

Krause, W., et al., "Contrast Agents: Magnetic Resonance Imaging—Relaxivity of MRI Contrast Agents", Topics in Current Chemistry, 2002, copyright 2002 Springer-Verlag Berlin Heidelberg, Germany.

"Toxicological Profile for Cobalt", U.S. Department of Health and Human Services, Public Health Service, Agency for Toxic Substances and Disease Registry, Apr. 2004.

Woo, R.K., et al., "Chapter 1—Biomaterials: Historical Overview and Current Directions", Nanoscale Technology in Biological Systems, CRC Press, copyright 2005 by Taylor & Francis.

Lee, H.B., et al., "Polymeric Biomaterials", The Biomedical Engineering Handbook: Second Edition, CRC Press LLC, 2000, Boca Raton.

Bolskar, R.D., et al., "Water-Soluble Gadofullerenes: Toward High-Relaxivity, pH-Responsive MRI Contrast Agents", Journal of the American Chemical Society, 2005, vol. 127, No. 2, pp. 799-805, American Chemical Society.

Solomon, I., "Relaxation Processes in a System of Two Spins," Physical Review, Jul. 1955, vol. 99, No. 2, pp. 559-565.

Butler, W.M. and Merrick, G.S., "Introduction to Prostate Brachytherapy," in: B.R. Thomadsen MJR, ed. Brachytherapy Physics 2nd edition, 2005, pp. 521-557.

Frank, S.J., et al., "An Assessment of Quality of Life Following Radical Prostatectomy, High-Dose External Beam Radiation Therapy, and Brachytherapy Iodine Implantation as Monotherapies for Localized Prostate Cancer," The Journal of Urology, 2007, vol. 177, No. 6, pp. 2151-2156, copyright 2007 American Urological Association.

Zelefsky, M.J., et al., "Multi-Institutional Analysis of Long-Term Outcome for Stages T1-T2 Prostate Cancer Treated With Permanent Seed Implantation," International Journal of Radiation Oncology, Biology, Physics, 2007, vol. 67, No. 2, pp. 327-333, copyright 2007 Elsevier Inc.

Merrick, G.S., et al., "Variability of Prostate Brachytherapy Pre-implant Dosimetry: A Multi-Instutional Analysis," Brachytherapy, 2005, vol. 4, No. 4, pp. 241-251, copyright 2005 American Brachytherapy Society.

Shah, J.N., et al., "Improved Biochemical Control and Clinical Disease-free Survival with Intraoperative Versus Preoperative Preplanning for Transperineal Interstitial Permanent Prostate Brachytherapy," Cancer Journal, 2006, vol. 12, No. 4, pp. 289-297.

Matzkin, H., et al., "Comparison Between Two Iodine—125 Brachytherapy Implant Techniques: Pre-planning and Intra-Operative by Various Dosimetry Quality Indicators," Radiotherapy and Oncology, 2003, vol. 68, No. 3, pp. 289-294, copyright 2003 Elsevier Ireland Ltd.

Han, B.H., et al., "The Effect of Interobserver Differences in Post-Implant Prostate CT Image Interpretation on Dosimetric Parameters," Medical Physics, 2003, vol. 30, No. 6, pp. 1096-1102, copyright 2003 The American Association of Physicists in Medicine.

Frank, S.J., et al., "Interstitial Implant Alone or in Combination with External Beam Radiation Therapy for Intermediate-Risk Prostate Cancer: A Survey of Practice Patterns in the United States," Brachytherapy, 2007, vol. 6, No. 1, pp. 2-8.

Merrick, G.S., et al., "Initial Analysis of Pro-Qura: A Multi-institutional Database of Prostate Brachytherapy Dosimetry," Brachytherapy, 2007, vol. 6, No. 1, pp. 9-15.

Sanda, M.G., et al., "Quality of Life and Satisfaction With Outcome Among Prostate-Cancer Survivors," New England Journal of Medicine, 2008, vol. 358, No. 12, pp. 1250-1261.

Bretonniere, Y., et al., "Solid-State and Solution Properties of the Lanthanide Complexes of a New Heptadentate Tripodal Ligand: A Route to Gadolinium Complexes with an Improved Relaxation Efficiency," Inorganic Chemistry, 2001, vol. 40, pp. 6737-6745, copyright 2001 American Chemical Society.

Tempany, C.M., et al., "MR-Guided Prostate Interventions," Journal of Magnetic Resonance Imaging, 2008, vol. 27, pp. 356-367, copyright 2008 Wiley-Liss, Inc.

D'Amico, A.V., et al., "Comparing PSA Outcome After Radical Prostatectomy or Magnetic Resonance Imaging Guided Partial Prostatic Irradiation in Select Patients With Clinically Localized Adenocarcinoma of the Prostate," Urology, 2003, vol. 62, pp. 1063-1067, copyright 2003 Elsevier Inc.

Roberson, P.L., et al., "Use and Uncertainties of Mutual Information for Computed Tomography/Magnetic Resonance (CT/MR) Registration Post Permanent Implant of the Prostate," Medical Physics, Feb. 2005, vol. 32, No. 2, pp. 473-482, copyright 2005 The American Association of Physicists in Medicine.

De Bazelaire, C.M.J., et al., "MR Imaging Relaxation Times of Abdominal and Pelvic Tissues Measured in Vivo at 3.0 T: Preliminary Results", Relaxation Times of Abdominal and Pelvic Tissues, Mar. 2004, vol. 230, No. 3, pp. 652-659, copyright 2004 RSNA.

Unger, E.C.S.D., et al., "Gadolinium-Containing Copolymeric Chelates—A New Potential MR Contrast Agent," MAGMA, 1999, vol. 8, No. 3, pp. 154-62, copyright 1999 Elsevier Science B.V.

Wen, X., et al., "Synthesis and Characterization of Poly(L-Glutamic Acid) Gadolinium Chelate: A New Biodegradable MRI Contrast Agent," Bioconjugate Chemistry, 2004, vol. 15, No. 6, pp. 1408-1415, copyright 2004 American Chemical Society.

Rivera, B., et al., "Canine Transmissible Venereal Tumor: A Large-Animal Transplantable Tumor Model," Comparative Medicine, Aug. 2005, vol. 55, No. 4, pp. 335-343, copyright 2005 American Association for Laboratory for Animal Science.

McNichols, R.J., et al., "Percutaneous MRI Guided Laser Thermal Therapy in Canine Prostate," SPIE, 2005, vol. 5686, pp. 214.

Kangasniemi, M., et al., "Dynamic Gadolinium Uptake in Thermally Treated Canine Brain Tissue and Experimental Cerebral Tumors," Investigative Radiology, 2003, vol. 38, No. 2, pp. 102-107, copyright 2003 Lippincott Williams & Wilkins, Inc.

Hazle, J.D., et al., "MRI-Guided Thermal Therapy of Transplanted Tumors in the Canine Prostate Using a Directional Transurethral Ultrasound Applicator," JMRI, 2002, vol. 15, No. 4, pp. 409-417, copyright 2002 Wiley-Liss Inc.

Diederich, C.J., et al., "Transurethral Ultrasound Applicators with Directional Heating Patterns for Prostate Thermal Therapy: In Vivo Evaluation Using Magnetic Resonance Thermometry", Medical Physics, Feb. 2004, vol. 31, No. 2, pp. 405-413, copyright 2004 The American Association of Physicists in Medicine.

Kangasniemi, M., et al., "Multiplanar MR Temperature-Sensitive Imaging of Cerebral Thermal Treatment Using Interstitial Ultrasound Applicators in a Canine Model", Journal of Magnetic Resonance Imaging, 2002, vol. 16, pp. 522-531, copyright 2002 Wiley-Liss Inc.

Ma, J., "Breath-Hold Water and Fat Imaging Using a Dual-Echo Two-Point Dixon Technique With an Efficient and Robust Phase-Correction Algorithm", Magnetic Resonance in Medicine, pp. 415-419, accepted Mar. 4, 2004, copyright 2004 Wiley-Liss, Inc.

Ma, J., "Multislice and Multicoil Phase-Sensitive Inversion-Recovery Imaging", Magnetic Resonance in Medicine, pp. 904-910, accepted Nov. 10, 2004, copyright 2005 Wiley-Liss, Inc.

Ma, J., et al., "Fat-Suppressed Three-Dimensional Dual Echo Dixon Technique for Contrast Agent Enhanced MRI", Journal of Magnetic Resonance Imaging, accepted Oct. 3, 2005, copyright 2006 Wiley-Liss, Inc.

Ma, J., et al., "Contrast agent enhanced breast imaging with a combined 3D dual echo Dixon and parallel imaging technique", Proc. Intl. Soc. Mag. Reson. Med. 14, 2006.

Ma, J., et al., "A fast spin echo two-point Dixon technique and its combination with sensitivity encoding for efficient T2-weighted imaging", Magnetic Resonance Imaging, accepted Oct. 16, 2005, copyright 2005 Elsevier Inc.

Son, J., et al., "Three-dimensional T1-weighted MR Imaging using a One-point Dixon Technique with Arbitrary Echo Time", Proc. Intl. Soc. Mag. Reson. Med. 13, 2005.

Ma, J., et al., "Silicone-Specific Imaging Using an Inversion-Recovery-Prepared Fast Three-Point Dixon Technique", Journal of Magnetic Resonance Imaging, pp. 298-302, accepted Oct. 30, 2003, copyright 2004 Wiley-Liss, Inc.

Ma, J., "Phase correction in two-point Dixon water and fat imaging using a three-dimensional region-growing algorithm", presented at the 12th annual scientific meeting of the International Society of Magnetic Resonance in Medicine, May 15-24, 2004, Japan.

Hubner, W., International Search Report for International Patent Application No. PCT/US2012/022092, dated Jul. 6, 2012.

Hubner, W., Written Opinion for International Patent Application No. PCT/US2012/022092, dated Jul. 6, 2012.

* cited by examiner

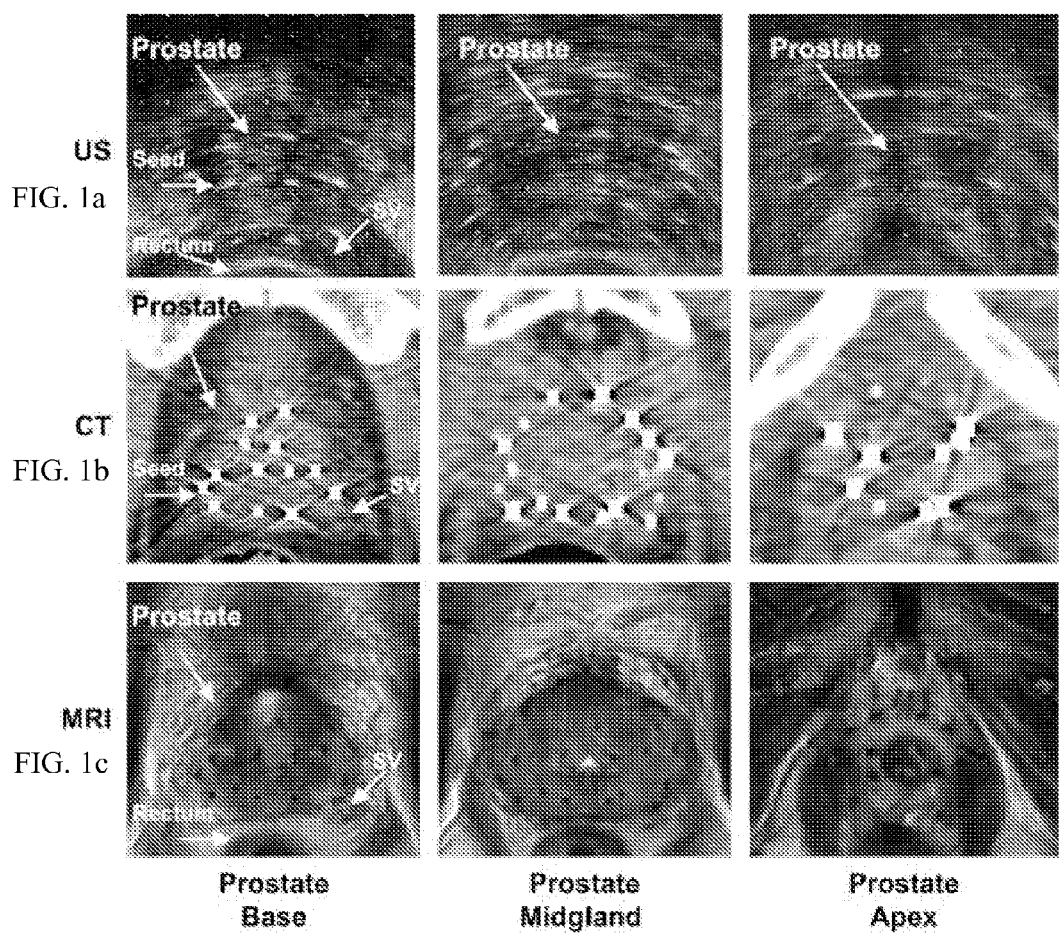

Note: Al or Au marker may be in any configuration within the seed with the radioactive material.

SEEDS AND MARKERS FOR USE IN IMAGING

CROSS-REFERENCE TO RELATED APPLICATIONS

This application claims priority to U.S. Pat. App. Ser. No. 60/949,157 filed Jul. 11, 2007. This application is incorporated by reference herein it its entirety.

FIELD OF INVENTION

The present invention relates generally to the magnetic resonance imaging (MRI) and more specifically, contrast agents and markers and methods of the same.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

BACKGROUND OF THE INVENTION

Magnetic resonance imaging ("MRI") is the optimal imaging modality for the prostate and surrounding critical organ structures. However, with MRI, the standard titanium radioactive seeds, strands of seeds, and needle tracks appear as black holes (negative contrast) and cannot be accurately localized within the prostate and periprostatic tissue. Without adequate localization of the radioactive seeds, MRI-based dosimetry is inaccurate, and therefore, MRI is not used in treatment planning, treatment delivery, or postimplant treatment quality evaluation. For example, brachytherapy titanium encapsulated seeds appear as negative contrast as well as any spacers and needle tracks. In turn, the seeds limit the ability to perform functional imaging of the prostate as the dosimetry cannot be accurate without positive identification of the seed.

MRI-CT fusion has been shown to improve postimplant quality assessment over CT alone, but this combined imaging approach has not been translatable to the community setting owing to inadequacies of fusing caused by imaging with different bladder and rectal filling, prostate volumetric differences between imaging modalities, and difficulties fusing the negative contrast of the seeds, strands of seeds, and needle tracks with the seeds visualized on CT scan. Crook, J., et al., *Interobserver Variation Inpostimplant Computed Tomography Contouring Affects Quality Assessment of Prostatebrachytherapy*, Brachytherapy, 2002, 1(2):66-73.

The consequence of the current inadequate ultrasound and CT imaging is subjective dosimetric evaluation and poor quality assurance during and after brachytherapy. Poor-quality implants are of critical clinical importance because they lead to decreased cure rates and increased side effects after treatment. Therefore, there is a critical need for national standardization of prostate brachytherapy dosimetry. This effort may be achieved through the design of seed implants of improved design that incorporate high contrast imaging capabilities.

Furthermore, novel MRI pulse sequences and protocols have been inadequate in identifying all of the implanted radioactive seeds and is not an adequate replacement of CT for evaluating dosimetry. For example, a recent article by Bloch et al. have proposed the use of high-resolution contrast-enhanced MRI (HR-CEMRI) with an endo-rectal coil as a complement to a T2-weighted MRI data set for MRI as a single imaging modality for the postimplant dosimetric evaluation. However, 12% (CEMRI) and 29% (T2-weighted MRI) of the seeds were missing which can lead to large dose uncertainties and should not be tolerated for accurate clinical dose reporting.

SUMMARY OF THE INVENTION

A contrast marker that includes a casing and a novel contrast agent comprising transition metal complexes, disposed within the casing is provided. The contrast markers may be placed in a strand, with or without a therapy seed, to produce a seeded strand useful for imaging and in connection with brachytherapy. Also provided is novel methodology to determine the appropriate range of concentration of the contrast agent so as to modulate the signal intensity as it relates to the activity of the therapy seed.

Methods of making the novel contrast agent, contrast marker, a therapy seed and the seeded strand are also provided. To make the seeded strand, at least one therapy seed and/or contrast marker is positioned in the bore of the strand. An optional spacer may be included in the seeded strand between markers or therapy seeds or between a marker and a therapy seed. The seeds, strands and contrast markers may also be used in connection with radioactive tracers.

In other aspects, methods of using the seeded strand by administering to a patient in need thereof the contrast marker, therapy seed, and/or seeded strand and imaging the patient to determine the position of the therapy seed and facilitating optimized radiation treatment are provided. Further, methodology for using MRI contrast agents as contrast markers and, more generally, as contrast agents/markers of biocompatible devices (both therapeutic (therapeutic and non-therapeutic) is taught herein in order to identify the precise location of an implanted device in vivo to maximize the therapeutic ratio. Both known and novel contrast agents are taught for use in such novel methodologies.

Methods of using magnetic resonance imaging ("MRI") in the planning, treatment, and post-implant evaluation for brachytherapy for disease in various organs including prostate, head and neck, breast, lung, brain, GI malignancies, sarcoma and the like are also provided herein. These methods include real-time MRI-guided prostate brachytherapy.

The foregoing has outlined rather broadly the features of the invention in order that the detailed description of the invention that follows may be better understood. Additional features and advantages of the invention will be described hereinafter, which form the subject of the claims of the invention.

DETAILED DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which:

FIG. 1a shows postimplant axial images of the prostate with ultrasound.

FIG. 1b shows postimplant axial images of the prostate with CT.

FIG. 1c show postimplant axial images of the prostate with MRI.

FIGS. 31a-31f show a urinary sphincter and MRI provides superior imaging of this critical structure responsible for urinary continence. It extends within the genitourinary diaphragm to the verumontanum within the prostate (a-f). McLaughlin, P. W., et al., *Functional Anatomy of the Prostate: Implications For Treatment Planning*, International Journal of Radiation Oncology Biology Physics, 2005, 63(2): 479-91.

Figure 32A:
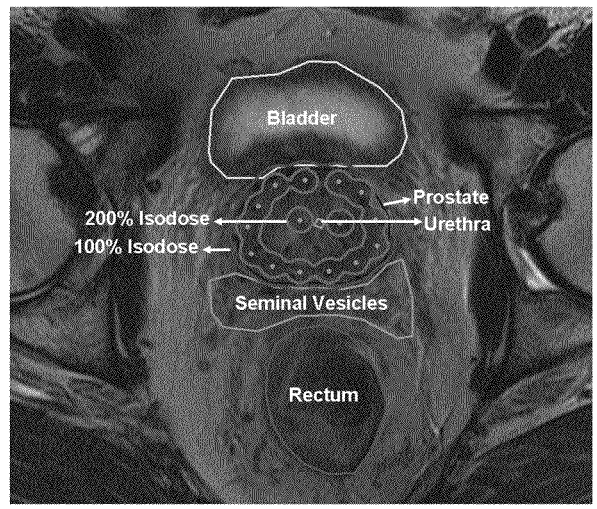
Figure 32B:
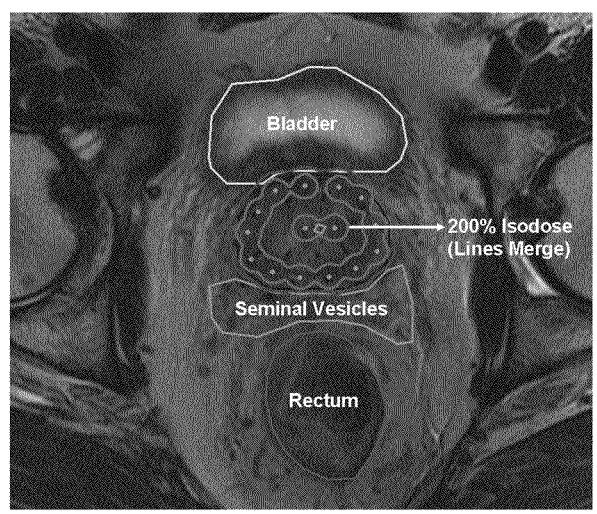
Figure 32C:
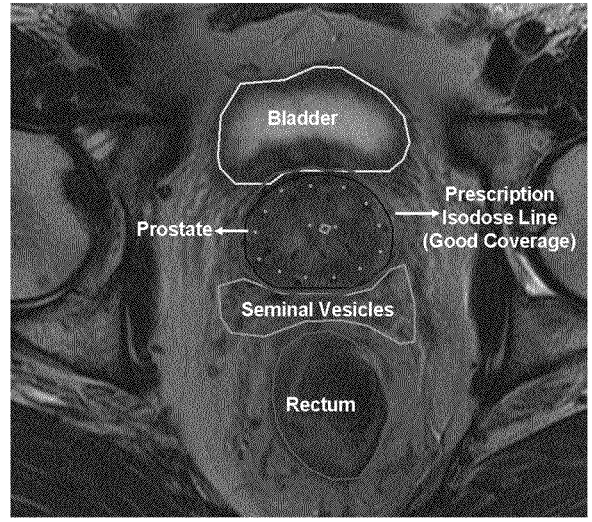
Figure 32D:
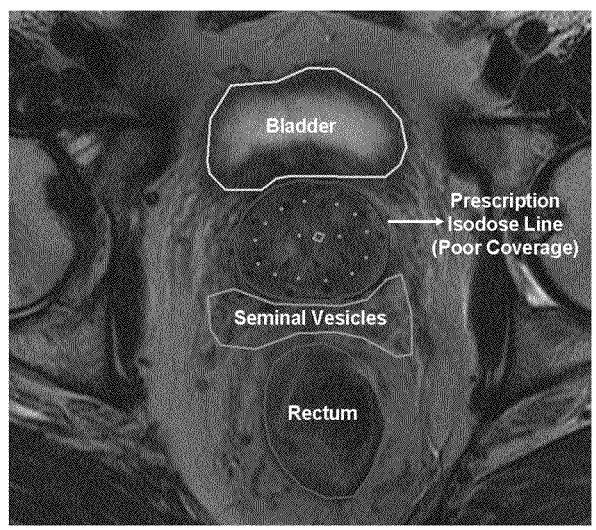

FIGS. 32a-32d illustrate the importance of seed placement accuracy. With a 2 mm misplacement of the periurethral implanted seeds medially, 200% of the prescribed dose overlaps the intraprostatic urethra (FIGS. 32a and 32b). With a 2-3 mm misplacement of peripherally loaded implanted seeds, the prescription isodose line was compromised leading to poor coverage of the prostate gland.

Figure 33:
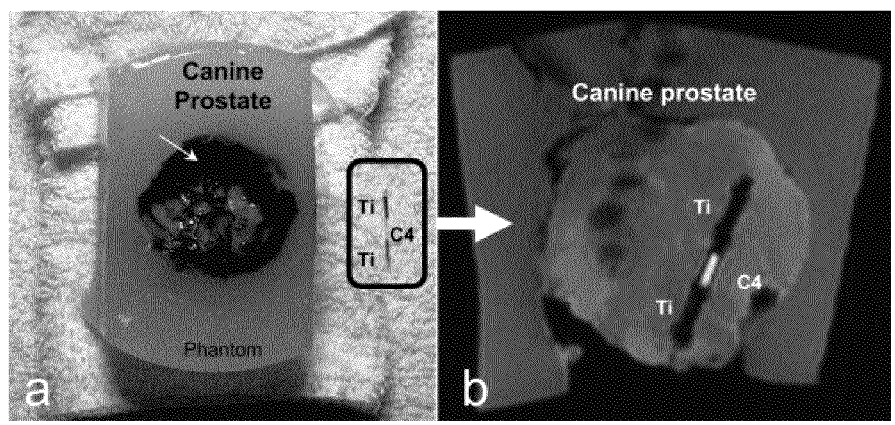

FIGS. 33a and 33b show that the ECAM having the contrast agent, C4 is able to positively identify the titanium (Ti) implanted seeds in an ex vivo canine prostate. Frank, S. J., et al., *A Novel MRI Marker For Prostate Brachytherapy*, International Journal of Radiation Oncology Biology Physics, 2008, 71(1):5-8.

Figure 34:
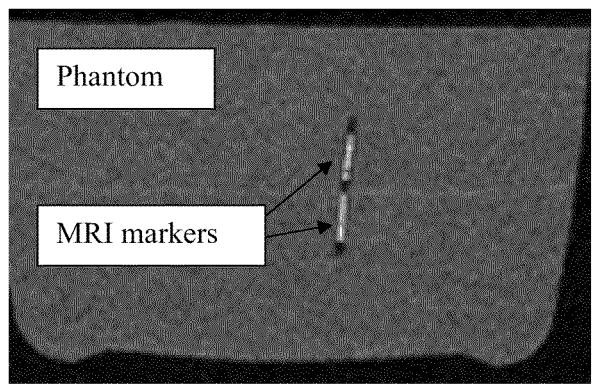

FIG. 34 shows an MRI image of the MRI visible marker by using biocompatible Poly(methyl methacrylate), (PMMA) and contrast agent, C4.

Figure 35A:
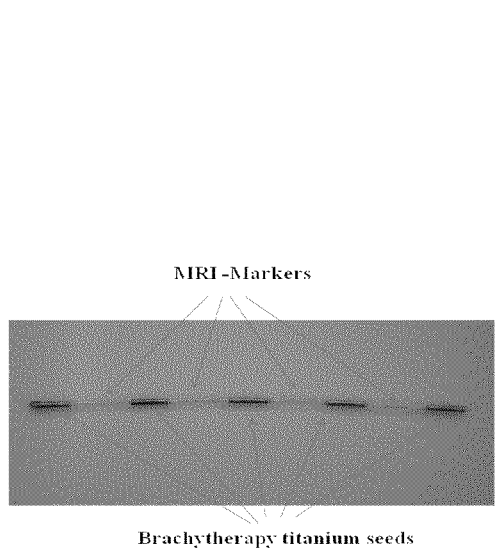

FIG. 35a shows a photograph of the MRI brachytherapy strand, also referred to herein as a seeded strand.

Figure 35B:
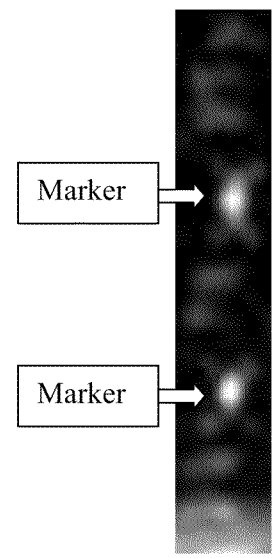

FIG. 35b shows a magnetic resonance image from MRI brachytherapy strand in phantom.

Figure 36:
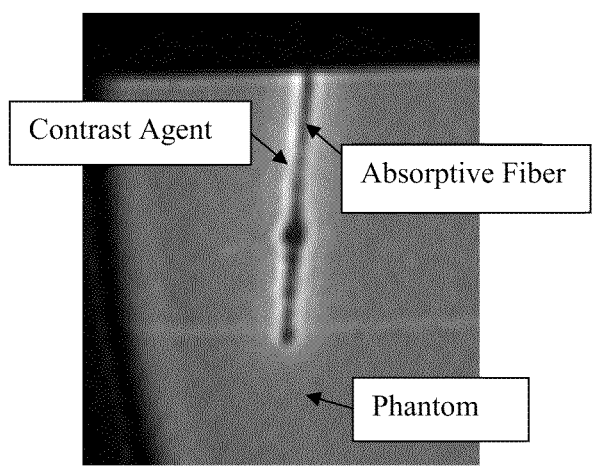

FIG. 36 shows an MRI image of the ECAM fabricated by using absorptive fiber, Magnevist contrast agent and PMMA/dichloromethane solution.

DETAILED DESCRIPTION

MRI is superior to ultrasound and CT in prostate gland delineation and surrounding critical organs like the rectum, urethra, and neurovascular structures. However, to date, individual therapy seeds and other medical devices are difficult to locate and/or identify using MRI, because the needle tracks, spacers, and seeds (particularly titanium seeds) appear as negative contrast. Frank, S. J., et al., *A Novel MRI Marker For Prostate Brachytherapy*, International Journal of Radiation Oncology Biology Physics, 2008, 71(1):5-8.

Figure 5:
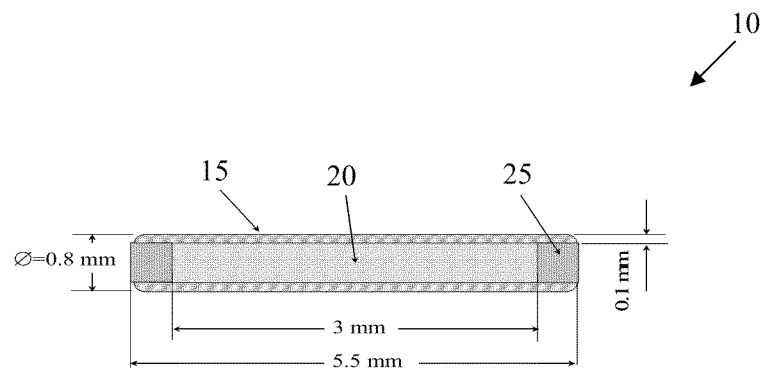
FIG. 5 shows a cross-sectional view of a contrast marker.
Figure 6:
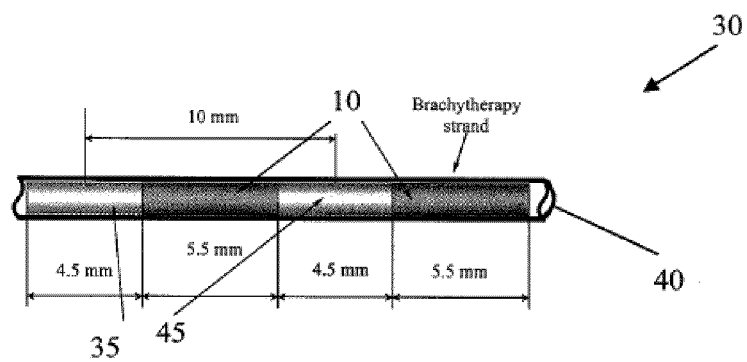
FIG. 6 shows a diagram of a therapy strand having contrast markers and therapy seeds.

Hence, a contrast marker 10 is provided that can be simply a contrast agent 20, or, the contrast marker 10 can be a medical device that has a casing 15 with the contrast agent 20 disposed within the casing 15 as shown in FIGS. 5 and 6. The contrast agent 20, also a type of medical device, is sometimes referred herein to as an "MR contrast agent" or "MRI contrast agent" and is useful alone as a contrast marker 10. The contrast agent 20 renders the contrast marker MRI-visible. The contrast marker 10 permits the accurate identification of an implanted radioactive therapy seed 35 and other medical devices in vivo, and facilitates the establishment of MRI-based brachytherapy dosimetry for prostate brachytherapy and other brachytherapies.

Alternatively the contrast agent 20 may be placed in the casing 15 that is not MRI-transparent, though in such markers the contrast agent 20 will generally be disposed on the outer surfaces of the casing 15. In this arrangement, the contrast agent 20 may be part of a "paint" or incorporated into a polymer matrix. Ideally, the casing 15 material may be chosen so that there is minimal interference with MRI signaling of the contrast agent 20.

Another medical device, a strand 30 is further provided. The strand 20 is capable of incorporating at least one contrast marker 10 and/or at least one therapy seed 35, or the combination of both contrast markers 10 and therapy seeds 35, resulting in what is sometimes referred to herein as an seeded strand 30. The seeded strand 30 may be made with a polymeric strand with a strand bore 40 in which said at least one contrast marker 10 is placed. The seeded strand 30 may also incorporate at least one spacer element 45, separating the contrast marker 10 from another contrast marker 10 and/or a therapy seed 35. Similarly, the spacer element 45 may separate therapy seeds 35 from one another. The spacer element 45 may be any material, including, but not limited to, water, solid titanium seeds, polymers such as polyethylene, polypropylene, polyamides, PTFE, polyester, polyurethanes, polyvinylchloride, PMMA, Polyetheretherketon (PEEK), or other biocompatible polymers, or contrast markers 10 and/or therapy seeds 35. The choice of material may be constrained only by the desire to not impede the quality of the MRI signal of the contrast agent 20. Spacer elements 45 may have dimensions that permit an accurate assignment of scale in an MRI image. Furthermore, the use of strands 30 that hold contrast markers 10 may be useful for the MRI assessment of brachytherapy strategies prior to the introduction of any radiation therapy seeds 35. This will be described in more detail below.

Seeded strands 30 may also contain just the contrast agent 20 or just the radioactive agent alone or within the contrast marker 10 and/or at least one therapy seed 35, respectively. Seeded strands 30 may contain a combination of therapy seeds 35 and contrast markers 10, or a combination of multiple markers, and/or multiple therapy seeds 35. A seeded strand 30 may also contain just radioactive agent alone or contrast agent 20 alone. Further, the seeded strand 30 may include a radioactive agent that may be disposed within a carrier substrate 50, such as the prototypical titanium seeds known in the art. The radioactive agent may be contained in the therapy seed 35 made with a casing 15 that is polymeric and non-metallic. Hence, the seeded strand 30 may be designed such that the strand bore 40 may be filled with contrast markers 10 only, therapy seeds 35 only or a combination of both. In addition, the contrast agent 20 and/or radioactive agent may be positioned within the strand 30. The seeded strands 30 may be ordered in any fashion deemed appropriate and may be optimized based on MRI assessments on an individualized patient using a planned brachytherapy approach (vide infra).

The seeded strand 30 may also include spacer elements 45. Spacer elements 45 may include any entity that would separate (i) therapy seeds 35 from each other, (ii) therapy seeds 35 from contrast markers 10, and (iii) contrast markers 10 from each other. The spacers may be any material, including water, or biocompatible polymer seeds. The choice of material for the spacer element 45 may be constrained only by the desire to not impede the quality of the MRI signal of the contrast agent 20.

The use of polyglycolic acid (pga) bioabsorbable synthetic material is suitable for the casing 15 and/or the strand 30. Therapy seeds 35 may contain radioactive agents such as Iodine-125, Palladium-103, Cesium-131, or Praseodymium-142 and/or contrast agents 20. Using this type of material, the contrast agent 20 may be visualized with MRI. Commonly used radioisotopes including iodine (I-125) and palladium (Pd-103), seeds may also contain other components such as X-ray imaging devices. See e.g., US Published Patent Application Number 2004/0109823, paragraphs [0006] and [0007] incorporated herein by reference.

The contrast agent 20 can be solutions with superparamagnetic, paramagnetic, or ferromagnetic properties. Through a modification process of the standard FDA approved brachytherapy strand, may incorporate MRI visible solutions in order to locate the radioactive therapy seed 35 within the prostate and periprostatic tissue. The pga synthetic strand may hold the therapy seeds 35, contrast markers 10 and/or MRI visible spacer elements 45 at discrete intervals within the strand 30. This improves the quality of the implant over individual loading the therapy seeds 35 by permitting the placement of the seeds in the periprostatic tissue to cover microscopic disease outside the capsule of the prostate. By placing therapy seeds 35 into the strand 30, migration of the seeds will not occur during the treatment. Fewer therapy seeds 35 and less activity may be used to achieve optimal dosimetry of the brachytherapy implant than loading individual therapy seeds 35.

For example, prostate cancer patients may be treated with a permanent radioactive brachytherapy seeded strand 30 using 50 to 120 seeds implanted into the prostate of the patient. MRI is an ideal imaging modality to visualize the apex, base, and later borders of the prostate. The anterior portion of the rectum and the prostate interface, as well as the seminal vesicle and base of the prostate interface, are well visualized with MRI as well. MRI-guided prostate brachytherapy may be performed, allowing for optimization of treatment. Following treatment, a MRI-visible seeded strand 30 will help determine the quality of the implant by verifying that the dosimetry is consistent with the prostate cancer treatment plan.

Advantageously, the MRI visible seed optimizes image guided radiation therapy with brachytherapy and minimizes the undesirable side-effects commonly associated with brachytherapy. Certain novel contrast agents provided herein have the general composition, $(CoCl_2)_n(C_2H_5NO_2)_{1-n}$. (where n=0.8-0.95) and are also referred to as "C4" or the "C4 complex." By a cobalt chloride complex contrast agent ("C4"), we have developed an encapsulated contrast agent marker ("ECAM") shows the location of the implanted radioactive seed in vivo using MRI. MRI contrast markers will provide clinicians the tool for a more accurate delivery of radiation treatment and is a device that can be used for other therapies such as either high-, low- or pulse-dose rate gynecologic, thoracic, intracranial, ocular, sarcoma, head and neck, and gastrointestinal.

MRI

In clinical MRI, the nuclear magnetic resonance signal from water protons in living tissue are used to image organs and disease sites, such as tumors, in 3D. The intensity of this MR signal depends on three important intrinsic tissue factors: the proton density, the longitudinal relaxation time, $T_1$, and the transverse relaxation time, $T_2$. Thus, various mathematical techniques have been developed to highlight the differences in $T_1$ or $T_2$ to obtain good contrast, ie, the difference in appearance of different tissues in an MR image. Otherwise, MR images would be fairly featureless since the amount of water does not vary significantly in the various tissues of in the body. (Balaji Sitharaman and Lon J Wilson Int J Nanomedicine. 2006 September; 1(3): 291-295).

MRI contrast agents as are used primarily to improve disease detection by increasing sensitivity and diagnostic confidence. Nearly all commercial CAs available today are ECF agents that distribute extracellularly and excrete exclusively via the kidney. There are several types of MRI CAs including extracellular fluid space (ECF) agents, extended-residence-intravascular agents (blood pool), and tissue (organ)-specific agents.

Contrast agents used in clinical MRI procedures operate by changing the proton nuclear spin relaxation times of water molecules in their vicinity, enhancing the detected MR signal in tissue (Lauffer 1987; Caravan et al 1999; Merbach et al 2001; Krause and Editors 2002). Thus, the most commonly used clinical contrast agents decrease $T_1$ relaxation times (also referred to as spin-lattice relaxation) of water protons in living tissue in the vicinity of the paramagnetic contrast agents. All contrast agents are paramagnetic (with unpaired electrons) because paramagnetic contrast agents generate very large lattice fields (magnetic and nuclear environments with which the protons interact during $T_1$ relaxation) in the immediate neighborhood of the contrast agent, which greatly shorten the $T_1$ of any water molecule that approaches the paramagnetic center.

The term "relaxivity" ($r_1$ for $T_1$ relaxation) is the determinant for evaluating the efficacy of any MRI contrast agent. The reduction in water relaxation times is normally linear with concentration the slope being known as relaxivity, a magnitude that reveals the net increase the longitudinal ($1/T_1$, $r_1$) or transversal ($1/T_2$, $r_2$) relaxation rates of water, produced by 1 mM solution of the contrast agent. It is defined as the change in the relaxation rate of the water protons per molar concentration of the paramagnetic contrast agent, and is expressed in units of $mM^{-1} sec^{-1}$. Gadolinium contrast agents used in current clinical use have a "relaxivity" $r_1 \sim 4$ $mM^{-1} s^{-1}$.

The high-spin paramagnetic gadolinium ($Gd^{3+}$) metal ion is the most effective $T_1$ relaxation agent. It has seven unpaired f-electrons, the greatest number of unpaired electrons exhibited by any atom or ion, a large magnetic moment ($\mu^2=63\mu_B^2$ where $\mu_B$ is the Bohr Magneton), and a highly symmetrical, slowly relaxing ground state ($^8S$-state) which produces strong oscillations near the $^1H$ Larmor frequency, and thus a strong $T_1$ effect.

Structures of known Gd-based MRI contrast agents include:

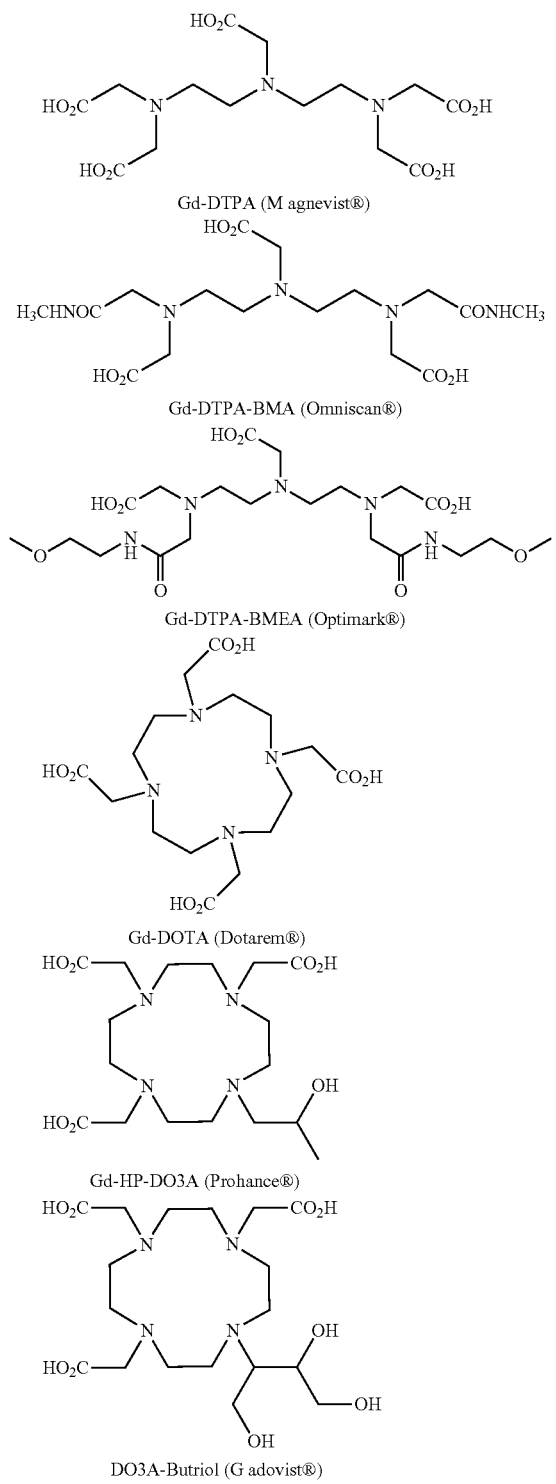

The aquated $Gd^{3+}$ ion is toxic, and therefore for medical use, its toxicity is usually sequestered by chelation with multidentate (linear and macrocyclic) ligands (Lauffer 1987;

Caravan et al 1999; Merbach et al 2001). Important increases in relaxivity were favoured by a deeper understanding of the theory of paramagnetic relaxation as proposed by Solomon, Bloembergen and Morgan. In general, theory indicated that to increase relaxivity it became necessary to increase the number of water molecules in the first coordination sphere of the metal ion (q, hydration number), to decrease its rotational correlation time ($\tau_c$), to favor faster water exchange ($k_{ex}$) on the complex, or a combination of these circumstances. Despite the impressive progress in the design and synthesis of $Gd^{3+}$ chelates for advanced CA applications, the resulting $Gd^{3+}$ complexes still possess limitations.

The novel cobalt-based MRI contrast agent (C4) with high T1 signal and a relaxivity ratio ($r_2/r_1$) of approximately 1.2 which makes it a good T1 contrast agent that may have less toxicity than Gd based agents because Cobalt is a natural component of vitamin B12.

Therefore, MRI contrast agents can be used as markers of biocompatible implanted devices (both therapeutic and non-therapeutic) in order to identify the precise location of the implanted device in vivo to maximize the therapeutic ratio (i.e. radioactive seed to positively identify to the millimeter where the radiation dose is being deposited). Specifically, the MRI contrast agent can identify the implanted radioactive seed and are not limited to the novel C4 agent. As discussed herein, other commonly used contrast agents using the appropriate calculated concentration necessary for the appropriate T1 relaxation time to optimize the positive contrast of the implanted radioactive seed or marker next to the seed by using the algorithms set out herein.

T1 is the longitudinal relaxation time. T2 is the transverse relaxation time. R1 (1/T1) is a relaxation rate. R2 (1/T2) is a relaxation rate. In determining correct concentration, what is important is the T1 time (ms). The shorter the T1 the greater the positive contrast between water (which has a higher T1). Here, each contrast agent has its different T2 relaxation times as well. If T1 is shortened too much, this may in turn, shorten the T2 too much and result in lost of positive contrast. Therefore, there is a balance between decreasing the T1 and not allowing the T2 to decrease too much. Hence, each MR imaging protocol can be optimized to the contrast agent of choice.

In summary, the relaxivity is a characteristic of the agent. Once the T1 relaxation times of the C4 agent were determined, the concentration of the Gad agents required to achieve similar T1 relaxation times was determined. This concentration was then tested and found to have positive contrast inside a polymer casing (PEEK, PMMA).

While it is known to use the relaxivity and relaxation rate (1/relaxation time) to come up with appropriate concentration range to optimize intravenous (IV) contrast agents, this course of action has not been used to optimize the contrast difference between an organ of interest and its surrounding structures. One reason it has not been done before is that the techniques are very different as well as the objectives. For example, gadolinium and its derivatives have been primarily used as an IV contrast agent but now with the methodology provided herein, may be used as MRI positive contrast agents as encapsulated markers.

Clearly, what is not known was to identify the appropriate concentration range for Gadolinium and its derivatives that gives the similar T1 relaxation time and positive contrast as the novel C4 agent. While this is true for contrast agents like Manganese that follow the Solomon, Bloembergen and Morgan principle, Gadolinium nanotubes do not follow the Solomon, Bloembergen and Morgan principle and further investigation will identify the optimal concentration range and sequencing protocols. The concentration necessary to achieve a positive contrast signal via T1 relaxation times for an encapsulated MRI marker in a polymer casing had not been adequately defined to date. Similarly, we were able to figure out that you could not place the contrast MRI marker inside a titanium seed due to the ballooning artifact and loss of signal from the susceptibility artifact. Therefore, in order to develop an MRI visible radioactive seed, a polymer radioactive seed with the MRI marker adjacent, inside or around the casing, or a titanium radioactive seed with the MRI marker adjacent to the seed. must be used.

Moreover, to optimizing concentration of the MR contrast agent, the T1 relaxation times of the C4 agent was used and by working backwards, the appropriate concentrations of other positive contrast agents that generate similar T1 relaxation times were identified. Other contrast agents may or may not have as strong positive contrast signal depending on their inherent properties and T2 relaxation times.

In short, C4 as a positive MR contrast agent was developed. Other agents were not initially visible to due inappropriate concentrations being tested (we know that now) As shown by Grimm et al, placing the MRI contrast agent inside the titanium seed is not possible due to the ballooning artifact that obliterates the positive contrast signal. In order to identify a titanium seed, the encapsulated MRI marker (ECAM—encapsulated contrast agent marker) must be adjacent to the titanium seed. In order to identify a polymer seed, the contrast agent can be adjacent, inside, or encase the polymer seed (as a paste, paint, or solution). Following the MRI characterization of the C4 agent at 1.5 T, 3.0 T, and 7 T, we determined the T1 relaxation times of the C4 agent and its inherent relaxivities. Many would consider our relaxivity to be too low compared to Gadolinium ("Gad") or other Gad derivatives, meaning that we would need a greater concentration of the C4 agent to achieve similar T1 positive contrast. However, an increased concentration is not a problem because the toxicity profile of Cobalt is different from Gadolinium and Cobalt is a natural supplement of Vitamin B12. See, Toxicological Profile for Cobalt, U.S. Department of Health and Human Sciences, Public Health Service, April 2004. By identifying the T1 relaxation times, the concentrations of Gad and its derivatives that would provide similar T1 relaxation times and tested Magnevist as an encapsulated contrast agent could be determined. This methodology provides the foundation for using MRI contrast agent markers for the identification of implantable objects in vivo, especially at concentrations considered non-toxic if the contrast agent were to leak from the capsule into the surrounding tissues.

Methods of visualizing implanted radioactive seeds under MRI with contrast agents using: the C4 complex and other contrast agents, a polymer casing, C4 inside the polymer casing, C4 outside a casing, the contrast agent inside the therapy (radioactive or chemo agent) polymer seed, the contrast agent outside the therapy (radioactive or chemo agent) polymer seed, and the C4 agent (having properties that make it an ideal contrast agent with an $r2/r1=1.2$) are each disclosed herein.

Encapsulating the Contrast Agents with the Casing

As noted above, the contrast agent 20 can be encapsulated with a casing 15 to form the contrast marker 10. Contrast markers are also referred to herein as an "encapsulated contrast agent marker" or "ECAM." Casing 15 may be made of glass or one or more polymers such as polyethylene, polypropylene, polyamides, PTFE, polyester, polyurethanes, polyvinylchloride, PMMA, Polyetheretherketon (PEEK), each of which has been reported to be biocompatible. Woo, R. K., et al., *Biomaterials: Historical Overview and Current Directions, Nanoscale,* In: R. S. Greco FBPaRLS, ed. CRC Press, 2004, 1-24. Good mechanical properties and high melting temperature of these polymers make them an excellent choice as construction materials for implantable biomedical applications including prosthetic and dental materials, implants, dressings and extracorporeal devices (each being considered to be a medical device by the US Food & Drug Administration ("FDA")). Lee, H. B., et al., *Polymeric Biomaterials*, In: J. D. Bronzino B R, ed. The Biomedical Engineering Handbook— CRC Press, 1995. Overall, polymeric biomaterials display several key advantages. These include ease of manufacturing into products with a wide variety of shapes, reasonable cost, wide availability, and wide variety of mechanical and physical properties. Shasti, V. P., *Non-Degradable Biocompatible Polymers in Medicine: Past, Present and Future*, Current Pharmaceutical Biotechnology, 2003, 4(5):331-37.

For MRI applications, low electrical conductivity of these types of polymers make the capsules transparent for high radio frequency signals. The schematic diagram of the proposed contrast marker 10 is shown in FIG. 5. The polymer tube can be processed to obtain hollow cylinders up to 5.5 mm in length, 0.8 mm in outer diameter (OD), and 0.6 mm in inner diameter (ID). One polymer tap 25 can be fastened to one of the tube ends. The tap can be locally heated up to 300° C. to secure the conjunction. Selected contrast agents 20 can be injected into the polymer. A second tap can be fastened to the seed and heated to prevent leakage of the contrast agent 20.

Constructed contrast marker 10 prototypes have been evaluated by clinical and research MRI units in both high and low magnetic fields. The relaxivity of the novel contrast agents 20 at various concentrations were quantified at 1.5 T, 3.0 T, 4.7 T, and 7.0 T as well as the concentration of agent that will maximize the signal intensity present in the interstitial space between seeds and/or markers in the strands 30, facilitating identification and localization of seeds. Following the Solomon-Bloembergen-Morgan model, the overall relaxation rate ($R_1=1/T_1$, $R_2=1/T_2$) of solutions are determined by their native relaxation rates and the relaxivity (1/mMol/s) and concentration of the contrast agent 20. Bloembergen, N., et al., *Proton Relaxation Times in Paramagnetic Solutions. Effects of Electron Spin Relaxation*, The Journal of Chemical Physics, 1961, 34(3):842-50; Solomon, I., *Relaxation Processes in a System of Two Spins*, Physics Review, 1955, 99:559-65.

$$R_{1,post-contrast}=R_{1,native}+r_{1,agent}\rho_{agent}$$

$$R_{2,post-contrast}=R_{2,native}+r_{2,agent}\rho_{agent}$$

The contrast agents 20 were put into special NMR tubes, which fixed in a bath of relaxed water to minimize the effect of susceptibility mismatches on the measurements. T1 of the solutions evaluated using a saturation-recovery experiment. T2 and T2* measured using multi-echo gradient- and spin-echo sequences. Relaxation versus contrast agent 20 concentration data were fit to the above equations in a minimal mean-square error sense using Matlab (The Mathworks, Natick, Mass.).

Seeded Strands

A method of making the seeded strand 30 includes providing a polymer strand having a strand bore 40 and positioning at least one therapy seed 35 and/or contrast marker 10 in the strand bore 40. A typical therapy seed 35 includes a radioactive agent disposed within a carrier substrate 50. Additionally, one can position at least one contrast marker 10 in the strand as well as a spacer element 45 where deemed appropriate.

For integration of contrast markers 10 next to the therapy seeds 35, it is beneficial to use a flexible, biodegradable (polyglycolic acid) brachytherapy strand, such as those that can be purchased from BrachySciences Inc, Oxford, Conn. The standard strand typically has an internal diameter of 0.9 mm. This size is suitable for passing the contrast markers 10 and therapy seeds 35 through the strand bore 40. By using a needle having an interior diameter 0.84 mm the seeds can be set. FIG. 6 shows a schematic diagram of a loaded seeded strand with therapy seeds 35 (where titanium is used as the casing 15) and contrast markers 10.

As discussed in US Published Patent Application 2004/0109823, paragraphs [0030] through [0049], brachytherapy strands and methods of making are described as follows:

Brachytherapy strands typically have a size and shape suitable for passing through the bore of a needle having an interior diameter of less than about 2.7 millimeters (10 gauge), less than about 1.4 millimeters (15 gauge), less than about 0.84 millimeters (18 gauge), or less than about 0.56 millimeters (24 gauge). In one version, the strand is shaped into a cylinder having a diameter of between about 0.5 to 3 millimeters and a length of 20, 30, 40 centimeters or more.

Any appropriate biocompatible material can be used to form the brachytherapy seeds. Preferred materials include polymeric materials which are approved by the Food and Drug Administration for implantation.

In the preferred embodiment, the seeds are formed of a biodegradable material. Examples of suitable materials include synthetic polymers such as polyhydroxyacids (polylactic acid, polyglycolic-lactic acid), polyanhydrides (poly(bis(p-carboxyphenoxy)propane anhydride, poly(bis(p-carboxy)methane anhydride), copolymer of poly-carboxyphenoxypropane and sebacic acid); poly-orthoesters; polyhydroxyalkanoates (polyhydroxybutyric acid); and poly (isobutylcyanoacrylate). Other examples include open cell polylactic acid; co-polymers of a fatty acid dinner and sebacic acid; poly(carboxyphenoxy)hexane; poly-1,4-phenylene dipropionic acid; polyisophthalic acid; polydodecanedioic acid; poly(glycol-sebacate) (PGS); or other polymers described below. See, e.g., Biomaterials Engineering and Devices: Human Applications: Fundamentals and Vascular and Carrier Applications, Donald L. Wise et al. (eds), Humana Press, 2000; Biomaterials Science: An Introduction to Materials in Medicine, Buddy D. Ratner et al. (eds.), Academic Press, 1997; and Biomaterials and Bioengineering Handbook, Donald L. Wise, Marcel Dekker, 2000.

These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

In addition to synthetic polymers, natural polymers may also be used. In the preferred embodiment, the natural polymers are biodegradable. For example, tissue such as connective tissue from the walls of blood vessels or extracellular matrix may be used as a biodegradable carrier for delivery of radiation or another therapeutic substance. See, for example, U.S. Pat. No. 5,429,634 to Narcisco. Tissue may be autologous, heterologous, engineered, or otherwise modified so long as it is biocompatible with the target tissue. A patient may donate his own tissue to serve as a carrier for the therapeutic substance and/or radionuclide. Other tissues or natural polymers may serve as the degradable carrier matrices. For example, polysaccharides such as starch and dextran, proteins such as collagen, fibrin (Perka, et al., Tissue Eng. 7:359-361 (2001) and Senderoff, et al., J. Parenteral Sci. 45:2-6 (1991)), and albumin (see, for example, U.S. Pat. No. 5,707,644 to Ilum), elastin-like peptides, lipids, and combinations thereof. These materials can be derived from any of the sources known to those skilled in the art, including the patient's own tissues or blood.

Seeds or strands can also be made from synthetic or natural biocompatible non-polymeric and/or inorganic materials, which are preferably biodegradable. See for example, WO 99/53898 describing bioabsorbable porous silicon seeds and WO 00/50349 describing biodegradable ceramic fibers from silica sols. Other examples of non-polymeric and/or organic materials include: U.S. Pat. No. 5,640,705 to Koruga describing radiation-containing fullerene molecules; WO 02/34959A2 by Yeda Research and Development Co. Ltd. describing inorganic fullerene-like nanoparticles or structures; EP 1205437A1 to Osawa describing nano-size particulate graphite and multi-layer fullerene; U.S. Pat. No. 5,766,618 to Laurencin describing a polymeric-hydroxyapatite bone composite; GB 235140A to Asako Matsushima describing a ceramic composite such as hydroxyapatite for sustained release; and U.S. Pat. No. 5,762,950 to Antti Yli-Urpo disclosing a calcium phosphate, e.g. hydroxyapatite, bioactive ceramic for timed release.

In the case of radioactive seeds, it can be left to the clinician to select from any number of biodegradable carrier matrices which contain the radionuclide, so long as the degradation characteristics of the carrier substance are consistent with the desired absorption profile. This is because the carrier matrix itself will be sequestered from the surrounding target tissue along with the radionuclide until the radionuclide has decayed to an insignificant activity. At that time or afterwards, the biodegradable layer overlying the radioactive matrix will be eroded away, thus beginning a similar process for the now non-radioactive or nearly spent radioactive carrier.

In addition radioactive tracers may be optionally used as described in US Published Patent Application 2004/0109823, paragraphs [0040] through [0046] as follows:

Optionally, brachytherapy seed or strand can be imparted with a means of tracing the radioactive contents should those contents be released inadvertently.

Unforeseen problems associated with leakage of radioactive material, whether it be into the surrounding tissues in a patient, in a pathology lab, in a nuclear medicine lab, or in the operating room have been recently discovered as they relate to polymer seeds. The seed/strand should contain a means of tracing their contents should those contents be released inadvertently. This mechanism can rely on inclusion of fluorescent, luminescent, colored, pigmented or other approaches for tagging, detecting, or otherwise identifying the seed/strand contents either visually or with instrument assistance.

Fluorescence can be imparted using the appropriate polymer or other biodegradable substance, such as described by Sung in U.S. Pat. No. 4,885,254, Bryan in U.S. Pat. No. 6,416,960 B1, Barbera-Guillem in U.S. Pat. No. 6,548,171 B1, or Greiner in U.S. patent application Ser. No. 2003/0010508A1.

Luminescence can be imparted using the appropriate polymer or other biodegradable substance, such as described by Towns in WO 01/49768 A2, Sakakibara in EP 1 311 138 A1, Bryan in U.S. Pat. No. 6,436,682B1, Hancock in U.S. patent application Ser. No. 2003/0134959A1, or Wood in U.S. Pat. No. 6,552,179B1. Bioluminescence materials are described in U.S. Pat. No. 5,670,356. In addition, chemiluminescent and electroluminescent substances might be utilized, as well as other types of luminescent substances as would be known to one skilled in the art.

Quantum dots may also be loaded into the seeds and utilized to locate spilled substances from ruptured seeds/strands, like those described in U.S. patent application Ser. No. 2003/0129311 A1 or Dobson in WO 95/13891 (see also Jaiswal et al., Nature Biotechnology 2003; 21:47-51, and Quantum Dot Corporation's Qdot™ biotin conjugate).

Dyed biodegradable polymeric material may be used, as described by Burkhard in EP 1 093 824 A2. Other dyes can be used as indicated. Ultraviolet light can be utilized to detect a therapeutic agent like radioactive substances or drugs using a format described by Koshihara in U.S. Pat. No. 6,456,636 B1, or by Nakashima in WO 00/53659. Infrared dyes may be used, as described by Paulus in U.S. Pat. No. 5,426,143.

Those skilled in the art will be familiar with labeling, doping, or tagging the contents of the seeds/strands with agents that can be identified without modification, or pro-agents that can be identified by the addition of an activating substance or other means, such as labeled antibodies and the like.

Furthermore, other non-radioactive drugs can be used in combination with the strands. As described in US Published Patent Application 2004/0109823, paragraphs [0047] through [0049],

[p]olymers can be used to form, or to coat, drug delivery devices such as strands or strands containing any of a wide range of therapeutic and diagnostic agents. Any of a wide range of therapeutic, diagnostic and prophylactic materials can be incorporated into the strands, including organic compounds, inorganic compounds, proteins, polysaccharides, and nucleic acids, such as DNA, using standard techniques.

The non-radioactive drug can take the form of stimulating and growth factors; gene vectors; viral vectors; anti-angiogenesis agents; cytostatic, cytotoxic, and cytocidal agents; transforming agents; apoptosis-inducing agents; radiosensitizers; radioprotectants; hormones; enzymes; antibiotics; antiviral agents; mitogens; cytokines; anti-inflammatory agents; immunotoxins; antibodies; or antigens. For example, the non-radioactive therapeutic can be an anti-neoplastic agent such as paclitaxel, 5-fluorouracil, or cisplatin. It can also be a radiosensitizing agent such as 5-fluorouracil, etanidazole, tirapazamine, bromodeoxyuridine (BUdR) and iododeoxyuridine (IUdR).

Figure 13:
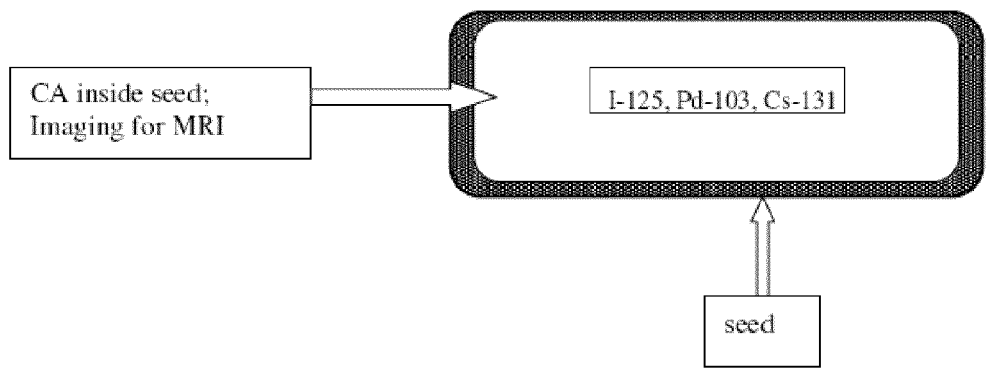
FIG. 13 shows a contrast agent inside the therapy seed.
Figure 14:
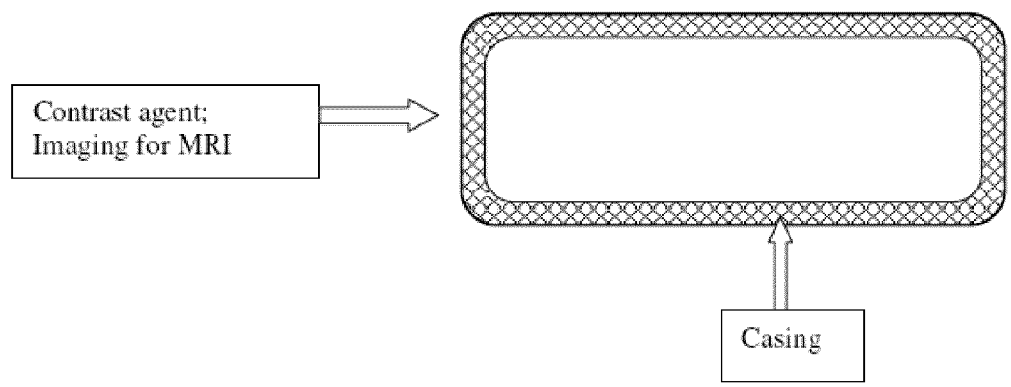
FIG. 14 shows the contrast agent mixed or coated with polymer around casing.
Figure 15A:
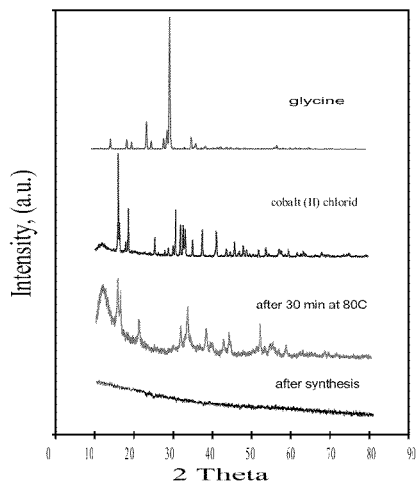
FIG. 15a shows X-ray diffraction patterns of as-synthesized, annealed and precursors, ($CoCl_2$ and Glycine).
Figure 15B:
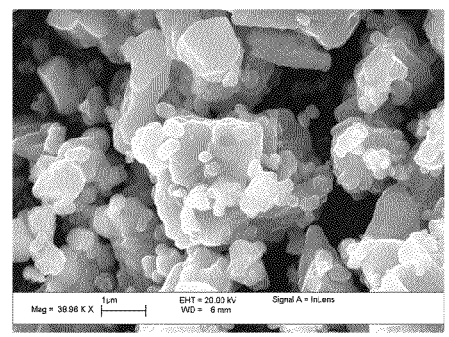
FIG. 15b shows the SEM image of annealed sample.
Figure 16A:
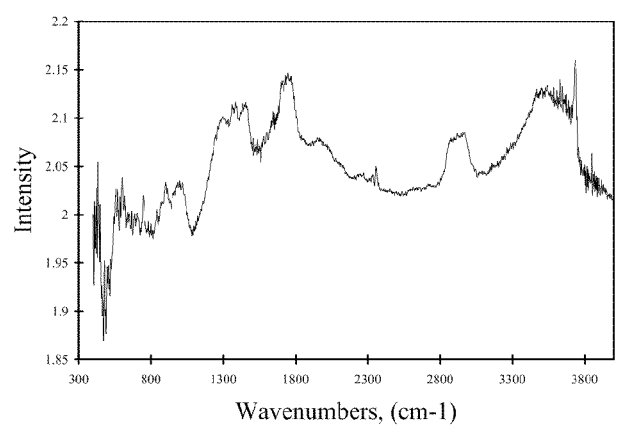
FIG. 16a shows a Fourier Transform Infrared spectroscopy of Co/glycine sample.
Figure 16B:
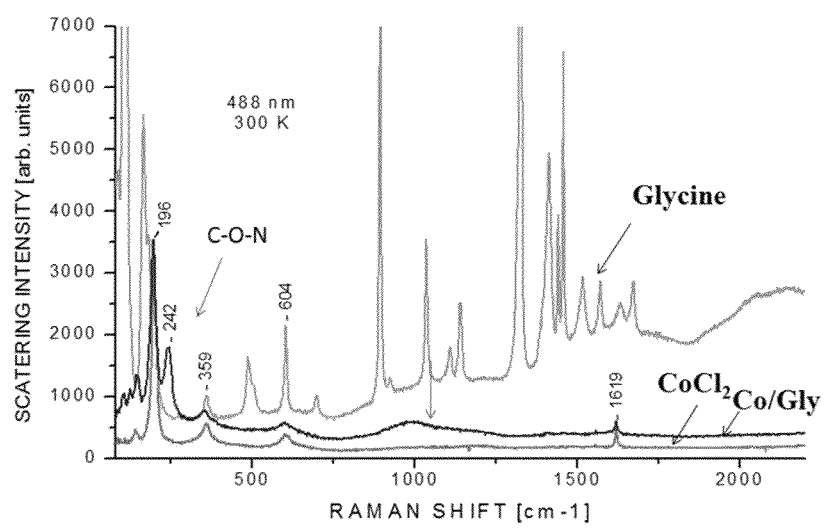
FIG. 16b shows a Raman spectroscopy of the cobalt complex identifies its unique chemical fingerprint.

Finally, in some aspects, the therapy seed 35 may incorporate contrast agents 20 as described above and shown in FIG. 13. Plastic therapy seeds 35 are known in the art and the contrast agent 20 may be incorporated into such FDA approved therapy seeds 35. Alternatively, the contrast agent 20 may be coated onto the outer surface of such therapy seeds 35. Thus, MRI-visible therapy seeds 35 are generated by incorporating contrast agents 20 allowing for direct detection of a therapy seed 35.

As described above, MRI visible seeded strands 30 by proxy use contrast markers 10 placed next to the therapy seeds 35 with a stranding material so that the therapy seed 35 will be readily identifiable under MRI due to its proximity to the contrast marker 10. The total length of the contrast marker 10 can be between 1 mm to 2.0 cm so that the unit of the therapy seed 35 plus the contrast marker 10 can vary, and the distance between consecutive therapy seeds 35 can also vary.

In the approach wherein the contrast agent 20 is part of the therapy seed 35 one can place about 0.3-1 µL of the contrast agent 20 into a typical plastic radioactive seed. No additional contrast marker 10 is required. The therapy seed 35 has standard dimensions with a length of about 4.5 mm. The therapy seed 35 may be implanted alone or in a seeded strand 30 (i.e. radioactive seed with predetermined spacers) format as disclosed hereinabove.

In other configurations, therapy seeds 35 may be coated with the contrast agent 20, or the contrast agent 20 may be incorporated into a stranding material (i.e. polyglycolic acid matrix) that is manufactured to coat the individual therapy seeds 35. About 15 µL of the contrast agent 20 can be used in such a coating process. The coated therapy seed 35 may be implanted alone or in combination with additional therapy seeds 35 and spacer element 45 in the seeded strand 30.

The contrast markers 10 and/or therapy seeds 35 may also include a carrier substrate 50 positioned within the casing 15. The carrier substrate 50 may be made with nanoparticles, or a single bulk material occupying a substantial fraction of the void volume of the casing 15. The carrier substrate 50 may be any material that can incorporate a radioactive therapeutic agent for use in radiation therapy. Radioactive therapeutic agents useful in connection with the subject invention include, but are not limited to, palladium-103, iodine-125, and cesium-131, Praseodymium-142. Also, contrast agents 20 may be absorbed on the surface of the carrier substrate 50. It may be possible to incorporate a radioactive therapeutic agent within the casing 15 itself, possibly obviating the need for the carrier substrate 50, except where it may be desirable, i.e., as a carrier of the contrast agent 20.

The seeds and markers described herein may be useful in treating a variety of diseases inflicting a variety of organs including heart, abdomen, head and neck, prostate, pancreas, liver, lung, brain, and breast, and for gynecological treatments. While the seeds and markers are useful in treating different types of cancers found in these organs, the markers and agents either together or alone maybe useful in diagnostic applications and other therapy applications. For all applications, where appropriate, the contrast agent can be coated onto a device, placed in a contrast marker adjacent to the device and/or placed inside a device.

For example, the contrast agent may be coated onto a seed, biopsy needles or MR-guided monitoring probes of thermal therapies (i.e. laser-induced, RF-induced, and cyromediated procedures) and used in the brain. Similarly, coronary stents, intravascular, IV catheter, guide wire and balloon catheters may be coated with the contrast agent. Prostrate applications include intraprostatic contrast agent, polymer needles, polymer catheters, fiducial marker on end of a catheter or needle, coating speed, coating spacer, fiducial marker next to see and HDR applicators.

For imaging the breast, the contrast agent could be used in connection with catheters (HDR, PDR and LDR), balloon catheters (HDR therapy) and as fiducial markers. Likewise, in other gynecological applications, the contrast agent may be used with tandem HDR applicators, or HDR or CDR catheter applicators. The contrast agent may also be useful in connection with an abdomen drain. The contrast agent is also useful in interventional radiology applications such as balloons, filters, drains, and stents.

Brachytherapy

Brachytherapy, also known as sealed source radiotherapy or endocurietherapy, is a form of radiotherapy where a radioactive source is placed inside or next to the area requiring treatment. Brachytherapy is commonly used to treat localized prostate cancer, cancers of the breast, and cancers of the head and neck.

Prostate brachytherapy is a nonsurgical standard-of-care approach for the treatment of prostate cancer. Patients who choose prostate brachytherapy do so because treatment consists of a 1-day outpatient procedure and cure rates are similar to if not better than those seen with surgery or external-beam radiation therapy. Butler, W. M., et al., *Introduction to Prostate Brachytherapy*, In: B. R. Thomadsen M J R, W. M. Butler, ed. Brachytherapy Physics 2nd Ed, 2005, 538:42. Additionally, patients treated with prostate brachytherapy almost always experience a higher quality of life, with less incontinence and better erectile function, than surgically treated patients. Frank, S. J., et al., *An Assessment of Quality of Life Following Radical Prostatectomy, High-Dose External Beam Radiation Therapy, and Brachytherapy Iodine Implantation as Monotherapies for Localized Prostate Cancer*, The Journal of Urology 2007, 177(6): 2151-2156.

Prostate brachytherapy is sought out by men diagnosed with cancer. Prostate radioactive seed implants, also know as brachytherapy, is a standard of care one-day outpatient treatment for approximately 30% of the 210,000 men annually diagnosed with prostate cancer. Outcomes following Brachytherapy are good but can vary significantly depending on the quality of the implant with an 8 year PSA relapse-free survival of 93% vs. 76% for high and low quality implants, respectively. Zelefsky, M. J., et al., *Multi-Institutional Analysis of Long-Term Outcome For Stages T1-T2 Prostate Cancer Treated With Permanent Seed Implantation*, International Journal of Radiation Oncology, Biology, Physics, 2007, 67(2): 327-333.

Hence, outcomes with high-quality prostate brachytherapy implants are good, but there is substantial heterogeneity between radiation oncologists institutions in the quality of implants. Although prostate brachytherapy prescription doses are uniform between institutions, there is significant variability regarding prostate treatment length, planning treatment volume, seed strength, dose homogeneity, treatment margins, and extracapsular seed placement. Merrick, G. S., et al., *Variability of Prostate Brachytherapy Pre-implant Dosimetry: A Multi-institutional Analysis*, Brachytherapy, 2005, 4(4):241-51. Experts have different opinions about whether or not to use a preplanning or intraoperative planning approach, how to evaluate the implant post-operatively with CT-based dosimetry, and which patients are appropriate candidates for brachytherapy alone versus a combination of external-beam radiation therapy plus brachytherapy. Shah, J. N., et al., *Improved Biochemical Control and Clinical Disease-free Survival with Intraoperative Versus Preoperative Preplanning for Transperineal Interstitial Permanent Prostate Brachytherapy*, Cancer Journal, 2006, 12(4):289-97; Matzkin, H., et al., *Comparison Between Two Iodine-125 Brachytherapy Implant Techniques: Pre-planning and Intra-Operative by Various Dosimetry Quality Indicators*, Radiotherapy and Oncology, 2003, 68(3):289-94; Han, B. H., et al., *The Effect of Interobserver Differences in Post-implant Prostate CT Image Interpretation on Dosimetric Parameters*, Medical Physics, 2003, 30(6):1096-102; Frank, S. J., et al., *Interstitial Implant Alone or in Combination with External Beam Radiation Therapy for Intermediate-Risk Prostate Cancer: A Survey of Practice Patterns in The United States*, Brachytherapy, 2007, 6(1):2-8. Owing to the subjective nature of post-implant quality evaluation with CT-based dosimetry, some community physicians have such difficulty evaluating the quality of their implants that they outsource their post-implant dosimetry to companies like ProQura in Seattle, Wash. to allow feedback from experts in the field (Seattle Prostate Institute). Among these physicians who outsource post-implant dosimetry—and by doing so indicate that they are concerned about quality and acknowledge the difficulty of post-implant evaluation—up to 25% of implants are found to be of poor quality. Merrick, G. S., et al., *Initial Analysis of Pro-Qura: A Multi-institutional Database of Prostate Brachytherapy Dosimetry*, Brachytherapy, 2007, 6(1):9-15.

Currently, the location of the titanium radioactive seeds used for prostate brachytherapy with respect to the tumor and normal critical organ structures remains ill defined with standard imaging modalities like ultrasound and computed tomography (CT) (FIG. 1*a-b*). Positive contrast of the titanium seeds on CT permit accurate localization of the seeds for post-implant dosimetry. However, these standard imaging modalities, which are used during treatment planning, treatment delivery, and post-implant treatment quality evaluation, provide inferior visualization of the prostate and surrounding critical organ structures, which leads to subjective determination of the quality of treatment.

Figure 30A:
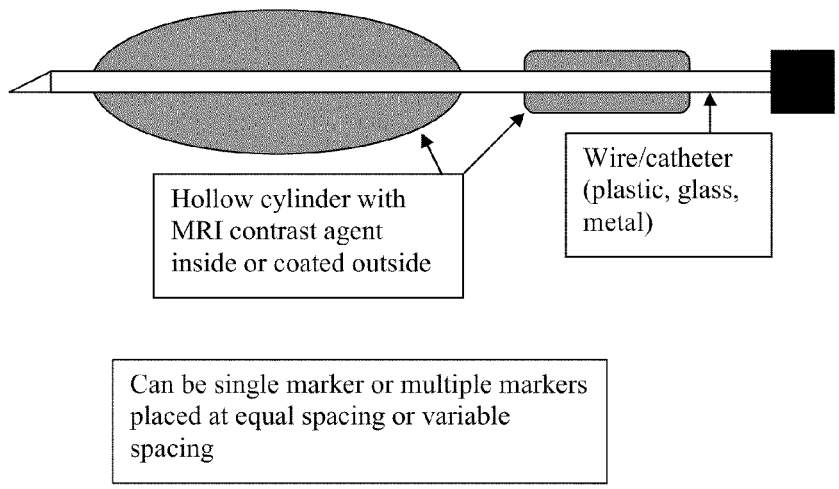
FIG. 30a depicts a hollow polymer seed with markers spaced in between during the manufacturing of the needle.
Figure 30B:
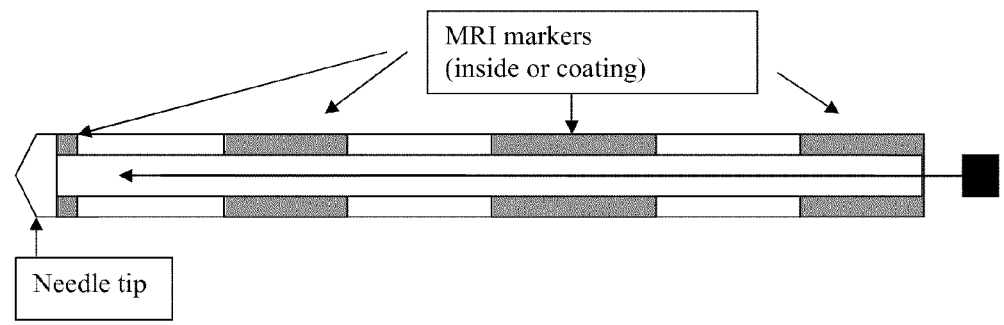
FIG. 30b shows an MRI marker having the contrast agent positioned inside a needle and/or coated outside.
Figure 31:
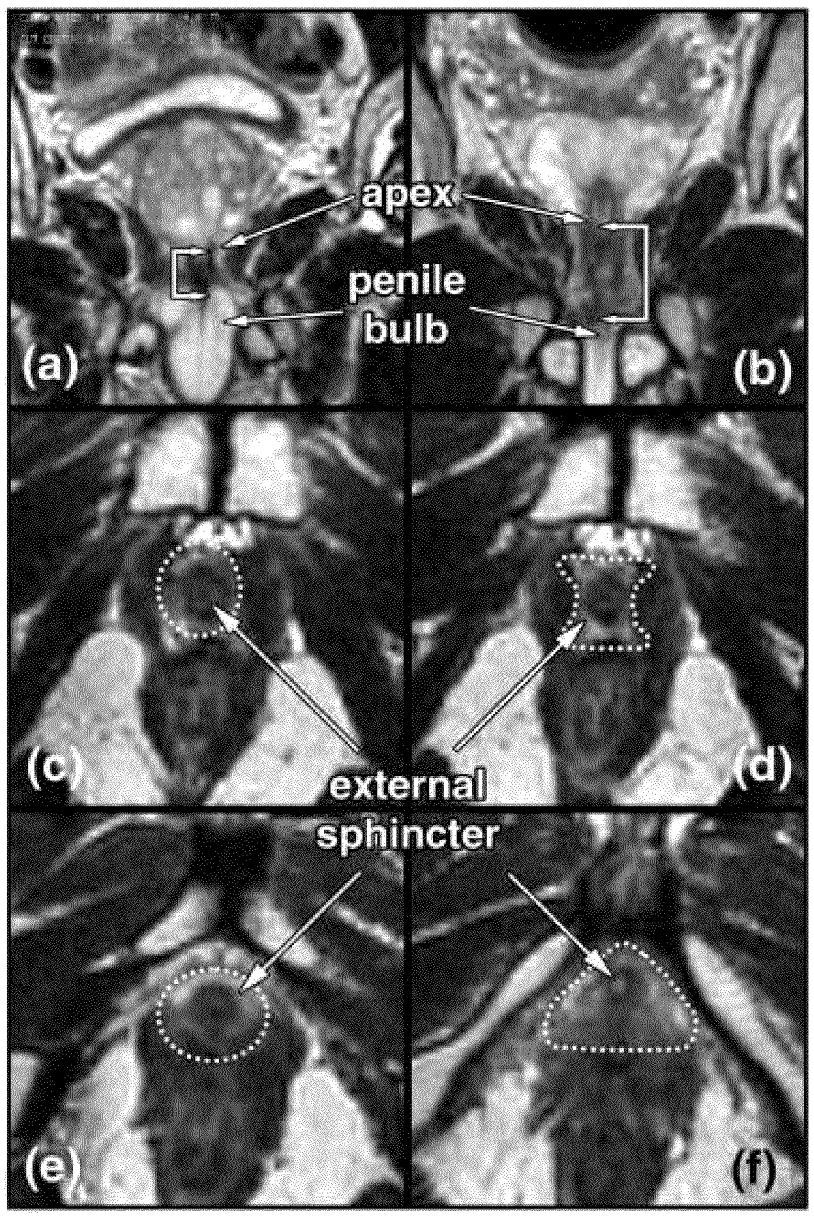

Urinary incontinence is a major health problem following treatment. Following treatment, men are often embarrassed if they leak urine, wet their pants, and wear diapers/pads. Recent data reveal that following brachytherapy, approximately 15% of men will experience incontinence 2 years and longer after their treatment. Sanda, M. G., et al., *Quality of Life and Satisfaction With Outcome Among Prostate-Cancer Survivors*, New England Journal of Medicine, 2008, 358(12): 1250-61; Frank, S. J., et al., *An Assessment of Quality of Life Following Radical Prostatectomy, High-Dose External Beam Radiation Therapy, and Brachytherapy Iodine Implantation as Monotherapies For Localized Prostate Cancer*, The Journal of Urology, 2007, 177(6);2151-6. The internal and external urinary sphincter cannot be adequately identified on standard imaging modalities (i.e. ultrasound, CT, or fluoroscopy) currently used for treatment, but these structures are well visualized on MRI (FIGS. 30 and 31). The use of superior imaging with MRI during the planning, treatment and post-treatment evaluation will result in improved cure rates and a decrease in complications following brachytherapy.

Increased accuracy of seed placement with MRI will improve outcomes. The current standard imaging solutions used for brachytherapy are suboptimal (FIG. 30). Frank, S. J., et al., *A Novel MRI Marker For Prostate Brachytherapy*, International Journal of Radiation Oncology Biology Physics, 2008, 71(1):5-8. Optimal imaging with MRI would improve the accuracy of seed placement thereby maximizing treatment efficacy and minimizing treatment related complications due to unnecessary radiation dose to the urinary sphincters (FIGS. 32*a*-32*d*).

MRI is the ideal imaging solution, but is currently limited by seed technology. MRI is the optimal imaging for the planning, treatment, and post-implant evaluation for brachytherapy and its efficacy has been well described. Tempany, C. M., et al., *MR-Guided Prostate Interventions*, Journal of Magnetic Resonance Imaging, 2008, 27:356-367; D'Amico, A. V., et al., *Comparing PSA Outcome After Radical Prostatectomy or Magnetic Resonance Imaging Guided Partial Prostatic Irradiation in Select Patients With Clinically Localized Adenocarcinoma of the Prostate*, Urology, 2003, 62:1063-1067. However, its use has been limited due to the inability to accurately identify the implanted radioactive seeds. Roberson, P. L., et al., *Use and Uncertainties of Mutual Information For Computed Tomography/Magnetic Resonance (CT/MR) Registration Post Permanent Implant of the Prostate*, Medical Physics, 2005, 32(2):473-82. All implanted seeds in the U.S. have radioactivity encased within a paramagnetic titanium shell. Under MRI, the implanted seeds in the prostate and periprostatic tissue appear as a negative contrast that is non-distinguishable from needle tracks and implanted seed spacers (FIG. 30). Additionally, artifacts generated through selected MR pulse sequencing protocols have not alleviated this problem. Attempts have been made to incorporate MRI in the post-implant evaluation through fusion of post-implant CT. Crook, J., et al., *Interobserver Variation in Postimplant Computed Tomography Contouring Affects Quality Assessment of Prostate Brachytherapy*, Brachytherapy, 2002, 1(2):66-73. However, differences in prostate gland size based on imaging modality, image registration variability due to different imaging tables (hardware) and differences in bladder and rectal filling, and excessive cost and inconvenience have decreased enthusiasm for MRI/CT fusion in the post-implant setting.

MRI-based brachytherapy transforms treatment from an "art" to a "science." On the surface, the innovation may appear modest, but the methods and devices presented herein are actually a technological advances within brachytherapy with the potential to significantly change the field by improving the quality of every implant that is performed. In the future, clinicians will have less anxiety about the quality of treatment delivered and during the MRI evaluation of treatment, if the prostate cancer is inadequately covered, additional seeds can be implanted to optimize treatment.

A systematic use of MRI brachytherapy provides a clinician the tools to perform consistent high quality implants. The use of MRI with ECAMs improves cure rates, decrease complications, and is ideal for the development of national standards for prostate brachytherapy.

For applications in brachytherapy, it can be desirable for the contrast marker 10 to have similar dimensional sizes to the a typical radioactive therapy seed 35 known in the art, so that the both contrast marker 10 and therapy seed 35 can be placed in a strand 30, creating an seeded strand 30. Due to the limited size of implantable contrast markers 10 (the typical dimensions of 5.5 mm in length and 0.8 mm in outer diameter (OD)) the volume of contrast agent 20 inside the contrast marker 10 should be less than 1 µL. The contrast agent 20 used as a contrast marker 10 has the following properties: (i) it should have a strong MRI signal to minimize damage that might be caused by leakage of the contrast agent 20; (ii) have a low electrical conductivity to be sufficiently transparent to high radio frequency; and (iii) should be biocompatible with human biochemistry.

MRI-Based Dosimetry Methodology

The following technique is for prostate implants but is not limited to such—similar planning, treatment and evaluation can be performed with GYN, Breast, Sarcoma, Lung, Brain, Heart or Kidney procedures using MRI.

Planning

Planning can be performed as "pre-planned" (i.e. prior to the patient arriving in the operating room/procedure room) or "intra-operative planning" (i.e. MRI-operative suite). A standard and/or functional MRI is performed at either low field (0.5 T, 1.5 T, 3 T) or high field (4.7 T, 7 T) with or without an endo-rectal coil. Various MRI protocols and imaging sequences with and without contrast (i.e. derivatives of T1- and T2-weighted) will be obtained to optimize identification of the treatment volume and normal organ structures. An ultrasound or CT may be obtained and transferred to the treatment planning system for fusion with MRI.

The DICOM images are transferred to a treatment planning software system. Template registration will be performed. The target volume and normal organ structures (rectum, bladder, penile bulb, urethra, neurovascular bundles, etc.) are contoured. The amount of activity (millicurie) per seed will be defined. The type of radioactivity used will be defined (Pd-103, I-125, Cs-131, etc.). The type of seed (vendor specific) will be defined. The type of material of seed will be defined (either titanium, plastic, glass, etc.) in order to determine where the MRI marker will be set in proximity to the seed to optimized identification of the seed. The seed itself may be MRI visible with the MRI marker inside. The ratio of MRI marker(s) to seed will be defined, with either a 1:1 ratio or 2:1 ratio. The distance of the MRI marker(s) to the center of the radioactive seed will be identified and entered.

Either manually or through inverse planning, the seeds with MRI markers are optimized to achieve dosimetric coverage of the target volume while minimizing dose to the critical organ structures. A dose volume histogram (DVH) can be obtained by observing the dose to all targets and organ structures for plan optimization. The amount of activity per target volume will then be evaluated to determine that appropriate treatment will be delivered.

The needle unit and MRI visible seeds/strands will be adequately sterilized. The needle unit will be loaded with the radioactive seeds and MRI markers as defined by the treatment plan. The needle can be made of a metal or polymer. The MRI visible radioactive seed can be a single unit or in a row of seeds attached by strand material. For quality assurance, prior to loading the MRI visible seeds into the needle unit, MRI imaging may be performed to verify that the MRI marker(s) to seed ratio is consistent with the treatment plan. The needle unit loading can be pre-loaded (i.e. prior to coming to the operating/procedure room) or intra-operatively loaded. If pre-loaded, the packaging should be such that there is adequate shielding for distribution. The needle unit may or may not be MRI compatible. The needle unit should be MRI compatible if the implant is in an MRI environment.

Treatment

The patient is brought to the operating/procedure room. The patient may or may not be under anesthesia. Quality assurance procedures are performed to verify the patient and the treatment, and to verify that the treatment plan is consistent with the patient and procedure. The needle loading will be verified with the planned MRI marker(s) per seed ratio or MRI visible seeds. The perineum of the patient will be prepped and draped in the standard fashion. The patient will have either an endo-rectal MRI coil placed or an ultrasound probe with the template placed next to the perineum. It is possible that the patient can have the implanting of the needles performed via ultrasound and then the needle(s) location verified with MRI prior to placement of the MRI visible seeds.

By using MRI in connection with prostate specification methodologies, needles can be implanted in real-time to the desired location as defined by the treatment plan. Real-time implementation provides for all of the needles to inserted as defined by the treatment plan and the MRI visible seeds immediately identified upon entry in vivo. The placement of the needles can be verified with respect to the location of the bladder, rectum, urethra, penile bulb, ejaculatory ducts, seminal vesicles, neurovascular bundles, etc. to prevent trauma to these normal structures to minimize the risk of morbidity. The MRI DICOM images can be immediately transferred to the treatment software with identification of the MRI markers. The dosimetric evaluation will be performed to optimize the patients treatment.

Post-Treatment Evaluation

Following the procedure, a standard and/or functional MRI will be performed at day 0 and/day 30 after the implant. A CT may also be performed to fuse with the MRI. The DICOM images captured will be transferred to the treatment system and the target volumes and normal organ structures will be contoured and delineated. The MRI markers will be manually or automatically identified. The dosimetric lines will be approximated to the radioactive seed which will have been predetermined based on the distance of the MRI marker(s) to the center of the radioactive seed. A dosimetric evaluation will be performed to verify that the target volume has been adequately treated as defined by the treatment plan. If the dose to the target volume is inadequate, optimization will be performed with the treatment software to determine the location of additional seeds with MRI marker(s) required. If seeds have been implanted too close to critical organ structures, an MRI compatible seed retrieval device can be used to remove the MRI visible seed(s).

Cobalt Contrast Markers

A novel contrast marker able to generate high intensity of $T_1$-weighted MRI signal is provided herein. This agent may be used to identify radioactive titanium and plastic seeds in prostate brachytherapy. The contrast agents provided herein are based on cobalt (II) chloride-glycine compounds with basic formula $(CoCl_2)_n(C_2H_5NO_2)_{1-n}$ where n=0.5-0.95, and characterize by VSM, XRD, SEM, and MRI. The aqua solution of (0.3-10%) $(CoCl_2)_{0.9}(C_2H_5NO_2)_{0.1}$ were incorporated into glass and polymer capsules and were well visualized by 1.5 T, 3 T, and 7 T MRI for quantities as low as 0.3 µL.

The ability of a T1-reducing contrast agent to generate a very bright signal against a background of normal tissue is a function of: (a) the relaxivity and concentration of the contrast agent; (b) the characteristic relaxation time constants of background tissues; and (c) the acquisition parameters of the MR imaging sequence.

Following the identification of the relaxivity properties of the novel agents, we were also able to show a similar contrast between encapsulated markers and surrounding tissues using the cobalt complex and clinically available MRI contrast agents such as Magnevist. In comparison to Magnevist, the relaxivity of the novel agents is lower, therefore, a higher concentration is required to achieve the T1 signal required.

Construction and Development of Novel Contrast Agents

Figure 2A:
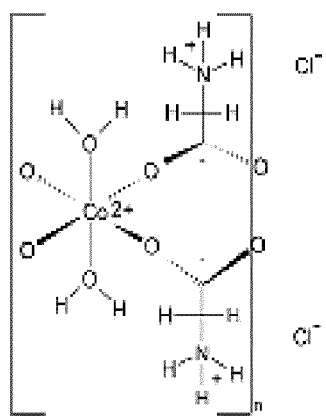
FIG. 2a shows novel contrast agents $(CoCl_2)_n(C_2H_5NO_2)_{1-n}$ where n=0.8 to 0.95. These contrast agents are sometimes referred to herein as "C4" and "C4 complex."
Figure 2B:
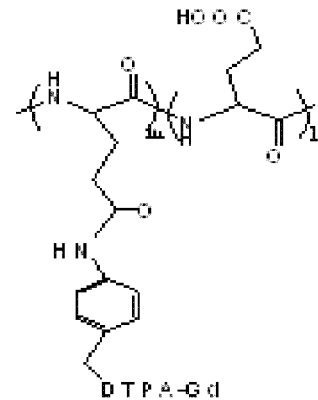
FIG. 2b shows the structure of the contrast agent L-PG-Bz-DTPA-Gd.

The contrast marker 10 includes contrast agent 20 that are metal complexes such as $[(CoCl_2)_{0.8}(C_2H_5NO_2)_{0.2}$ and L-PG-Bz-DTPA-Gd. Certain contrast agents 20 have been constructed and are found useful an MRI-visible contrast marker 10 with a high signal intensity on MRI. FIG. 2 shows the structures of the compound $[Co(C_2H_5NO_2)_2(H_2O)_2Cl_2]_n$ and L-PG-Bz-DTPA-Gd (average molecular weight 101,000). To develop these contrast agents 20, numerous agents were explored with paramagnetic, superparamagnetic, and weak ferromagnetic properties.

Contrast agents suitable for this invention include OMNISCAN™ (GE Healthcare, UK), OptiMARK, Magnevist, ProHance, and MultiHance FERIDEX I.V.® (Advanced Magnetics, Inc., Cambridge, Mass.), and colloidal nanoparticle solutions of $CoFe_2O_4$, Mn—Zn, Ni—Zn-ferrites, cobalt chloride, Fe—Co complex chloride, and cobalt (II) chloride-glycine compound with different concentrations.

The cobalt-glycine complexes such as $[C_2H_5NO_2]$ $CoCl_2.2H_2O$ and $[Co(C_2H_5NO_2)_2(H_2O)_2Cl_2]_n$ have been studied. Stenzel, K., et al., *Poly[[[diaquacobalt(II)]-di-µ-glycine]dichloride]*, Acta Crystallographica, 2004, 60(10): m1470-m72; Clegg, W., et al., *Structure of Three Glycine-bridged Polymeric Complexes: [Mn(glycine)(H2O)2Cl2], [Co(glycine)(H2O)2Cl2] and [Co(glycine)(H2O)4](NO3)2.*

*Acta Crystallographica, 1987, C43:794-97*. The main structural feature of compound $[Co(C_2H_5NO_2)_2(H_2O)_2Cl_2]_n$ is the coordination polyhedron of the Co atom on a center of inversion (FIG. 2a). MRI contrast agent 20 based on the $Co^{2+}$ ions were prepared using anhydrous cobalt (II) chloride and glycine reactants with stoichiometry of compound $(CoCl_2)_{0.8}(C_2H_5NO_2)_{0.2}$. The reactants were dissolved in deionized water and stirred at the temperature of 60° C. with a magnetic stir bar. The crystals of the $(CoCl_2)_{0.8}(C_2H_5NO_2)_{0.2}$, compounds were synthesized by slow water evaporation. To verify product homogeneity purity and magnetic ordering the products were characterized using XRD and SEM microprobe analysis. Water solutions (1-10 wt. %) with different cobalt (II) chlorides/glycine ratios were prepared for MRI testing.

Synthesis of the Cobalt Based Compounds $Co^{2+}$-based compounds were prepared using anhydrous cobalt (II) chloride ($CoCl_2$) and of amino acid-glycine ($H_2N(CH_2)CO_2H$) precursors. The precursors were purchased from Sigma Aldrich with purity (99+) and were used as received without further purification. The ratio among the reactants was set in the following stoichiometry of compound $(CoCl_2)_n(C_2H_5NO_2)_{1-n}$ where n=0.5-0.95.

Method 1. The (1.94-1.26 g) of cobalt chloride $CoCl_2$ (14.95-9.76 mmol) was added to 20 mL of double distilled water in a 100 mL Erlenmeyer flask, the solution was purple. Then, (0.732-0.059 g) of glycine (9.76-0.78 mmol) was dissolved in 10 mL of water in 50 mL flask. The cobalt chloride solution was added to the amino acid solution over a one-minute period. The mixture solution was stirred for the 30 minutes at 50 C. After slow evaporation of the solution for two days, pale purple rectangular crystals were obtained.

Method 2. The reactants (1.94-1.26 g) of $CoCl_2$ and (0.732-0.059 g) of glycine [$H_2N(CH_2)CO_2H$] were mixed and heated up to 160° C. in the nitrogen environment during 1 h. The synthesis yielded crystals of compound up to 5 mm.

Materials Characterization

The composition and crystal structure of the products were determined by X-ray diffraction (Siemens D5000 diffractometer) with Cu $K_\alpha$ radiation ($\lambda$=1.54056 Å).

The particle morphological features and microprobe analysis were determined by scanning electron microscopy (SEM; JEOL JAX8600, Japan) of loose powder fixed to a graphite disk. The sample was sputtered by graphite to enhance surface conductivity.

Analysis was performed using a Perkin Elmer 1600 Spectrometer with KBr beamsplitter, and MCT detector. The resolution was 4 $cm^{-1}$, with 64 co-added scans for the single-beam background and sample spectra. The spectral range was from 4000-400 $cm^{-1}$.

Raman scattering spectra of as-synthesized solid samples were measured at room temperature using HR640 spectrometer equipped with a microscope, notch filters, and a liquid-nitrogen-cooled CCD detector. The 488 nm laser line, focused with a ×50 objective on a spot of (~5 μm) diameter on the sample surface, were used for excitation.

Viscosity of contrast agent solution was measured at room temperature by using Brookfield digital viscometer DV-II.

The Fisher 21 tensiometer was used to measure surface tension of contrast agents with accuracy t within +/−0.25%.

Octanol-water partition coefficients ($P_{oct/wat}$) were measured by dissolving 10 mg of each compound in one milliliter of a 1:1 mixture of octanol and water. The resulting biphasic solution was shaken vigorously for two hours at which point 400 μL of the octanol layer and 400 μL of the water layer were removed. The solvent from each sample was removed under reduced pressure and the mass of the compound in the octanol sample was divided by the mass of the compound in the water sample. This experiment was repeated in triplicate, and the results were averaged to give the Log ($P_{oct/wat}$) values. All complexes were completely soluble in the mixture of octanol and water.

Magnetic Characterization

Superconducting Quantum Interference Device (SQUID): Magnetic properties of the Co-based compounds, such as saturation magnetization, blocking temperature, coercivity, remanence, and initial permeability were measured in a Quantum Design MPMS SQUID magnetometer over a broad range of temperatures (5 to 300 K and magnetic field up to 5 Tesla). In order to eliminate the interaction of the particles in the samples, the powder was dispersed in paraffin.

The magnetic properties of contrast agent solutions were determined by VSM (Vibrating Sample Magnetometer) at room temperature and magnetic field up to 1.5 T.

Structure and Properties of Co/Glycine Compounds:

X-ray patterns of as-synthesized sample produced by using method 1 (with precursors containing 9.76 mmol of $CoCl_2$ and 0.78 mmol of glycine) (FIG. 1, a) showed that product almost have amorphous structure, no reflection picks were recorded. However, further annealing at temperature 80 C, well crystalline structure is appeared. The morphology of the annealed product is shown in FIG. 1, b. As expected the powder is crystalline with broad particle sizes from 0.3 to 3 μm.

Fourier Transform Infrared (FTIR) spectrum of annealed sample is shown in FIG. 2. By interpreting the infrared absorption spectrum, the chemical bonds in a molecule can be determined. FTIR spectra of pure compounds are generally so unique that they are like a molecular "fingerprint". While organic compounds have very rich, detailed spectra, inorganic compounds are usually much simpler.

Magnetic Properties of Solid Compounds

Figure 17:
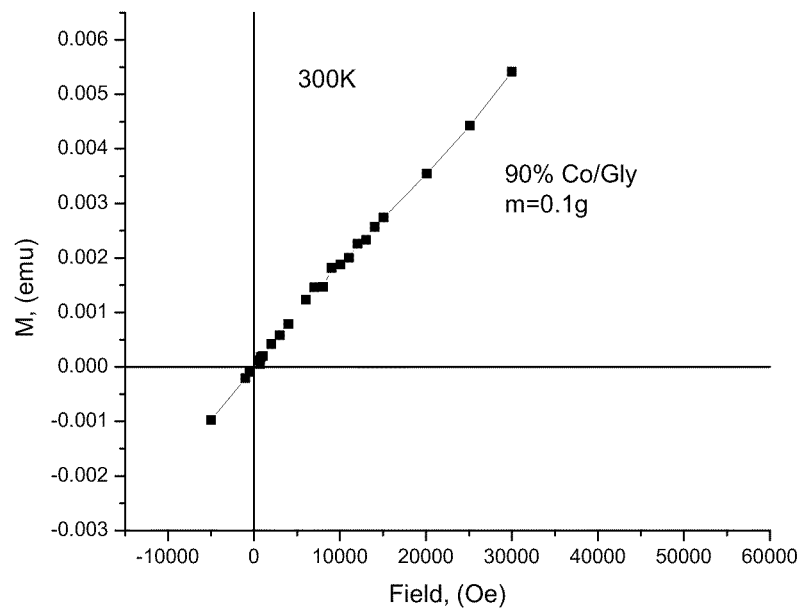
FIG. 17 shows a magnetization plot at 300 K of annealed sample.
Figure 18A:
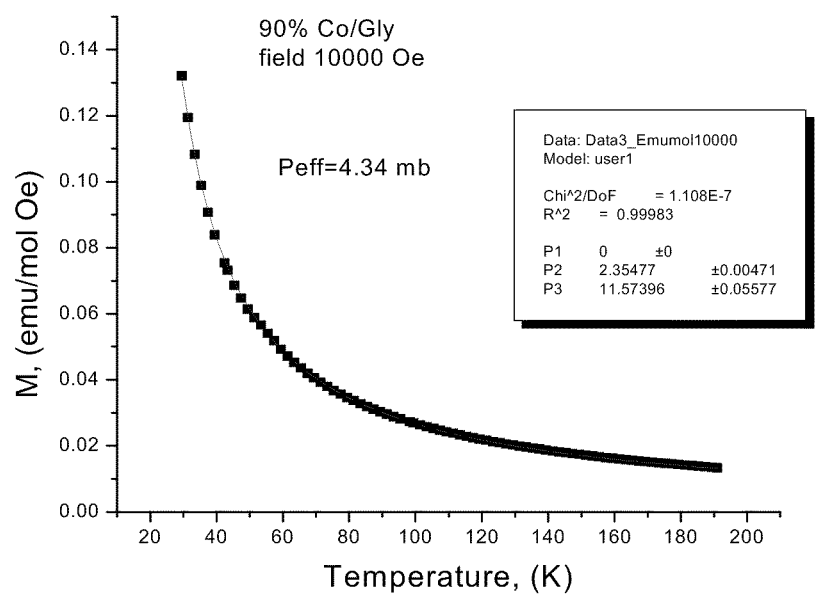
FIGS. 18a-18d depict the temperature dependence of the magnetization of the annealed sample and hysteresis loop.
Figure 18B:
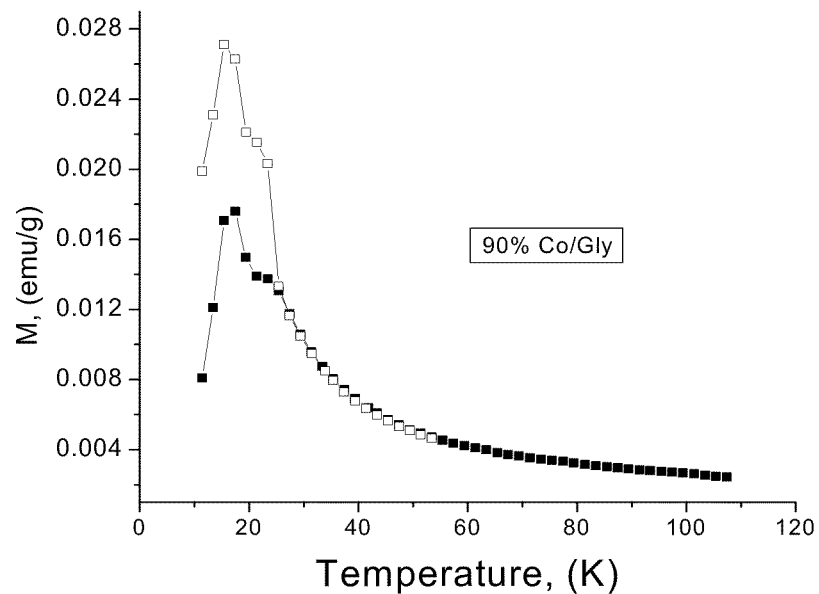
Figure 18C:
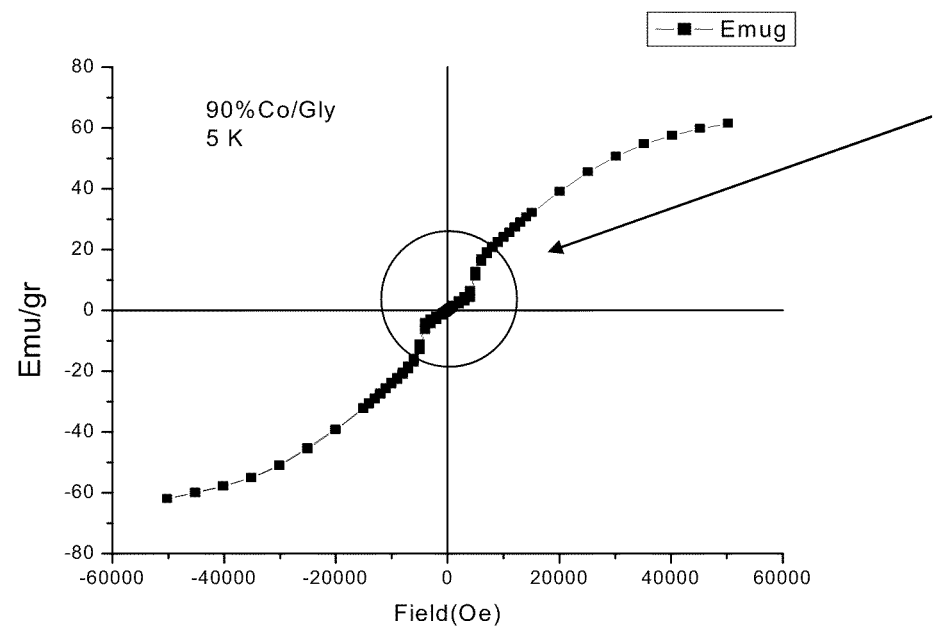
Figure 18D:
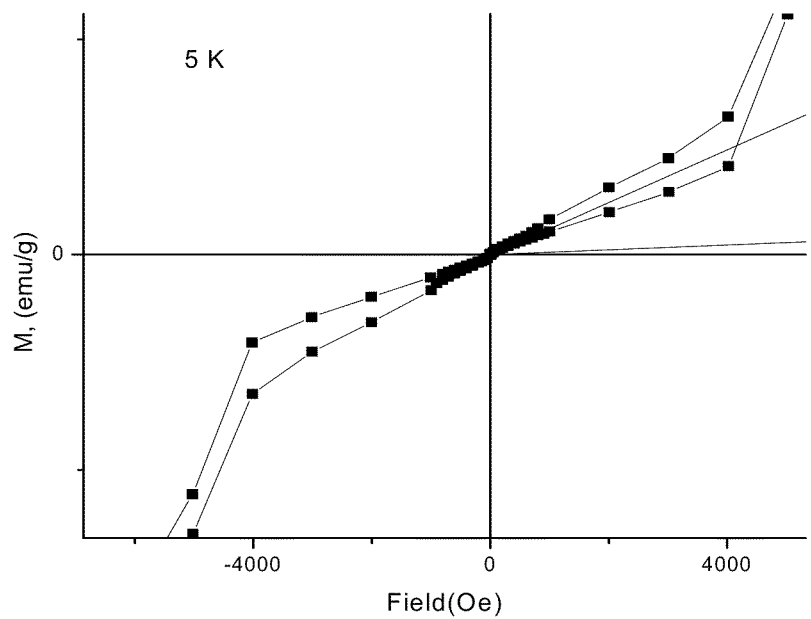

As shown in FIG. 17, the magnetization M(H) plot at 300 K of the as-synthesized and annealed samples (FIG. 17) indicate a paramagnetic properties.

The temperature dependence of the magnetization of the annealed, sample and hysteresis loop (measured at 5K) are shown in FIG. 18. The measurements show the antiferromagnetic behavior at the temperature less than 23 K and calculation of the effective magnetic moment by Curie-Weiss approach confirmed $P_{eff}$=4.34 MB. The hysteresis loop confirms the metamagnetic transition from paramagnetic to antiferromagnetic at low magnetic field.

Contrast Agent Properties

For preparation of aqua solution of contrast agent, the as-synthesized cobalt/glycine crystallites were dissolved in distilled water (0.3-10 wt %) and stirred at the room temperature with a magnetic stir bar for 1 h and then sonicated for 30 min.

Figure 19:
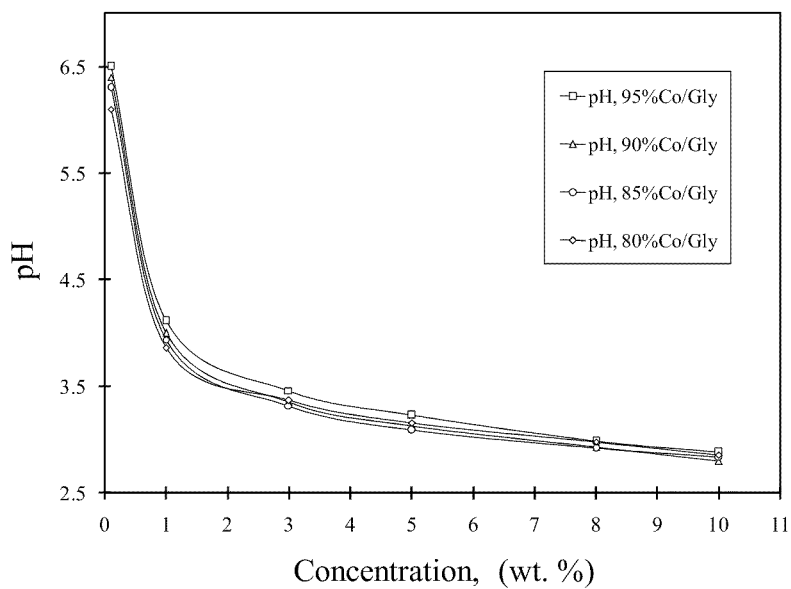
FIG. 19 shows the pH value of aqua solution of various Co/glycine aqua solutions.
Figure 20A:
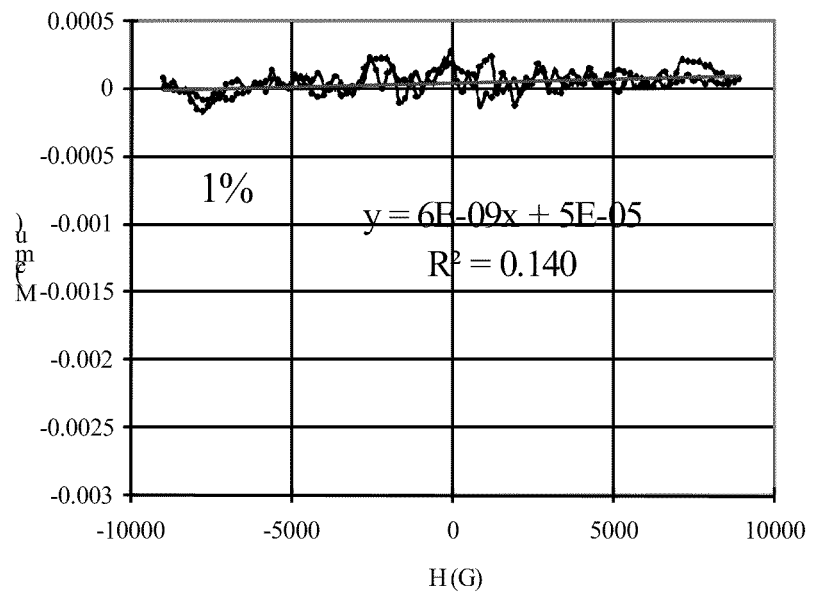
FIGS. 20a-20e depict the magnetic properties of aqua solution of Co/glysine compound.
Figure 20B:
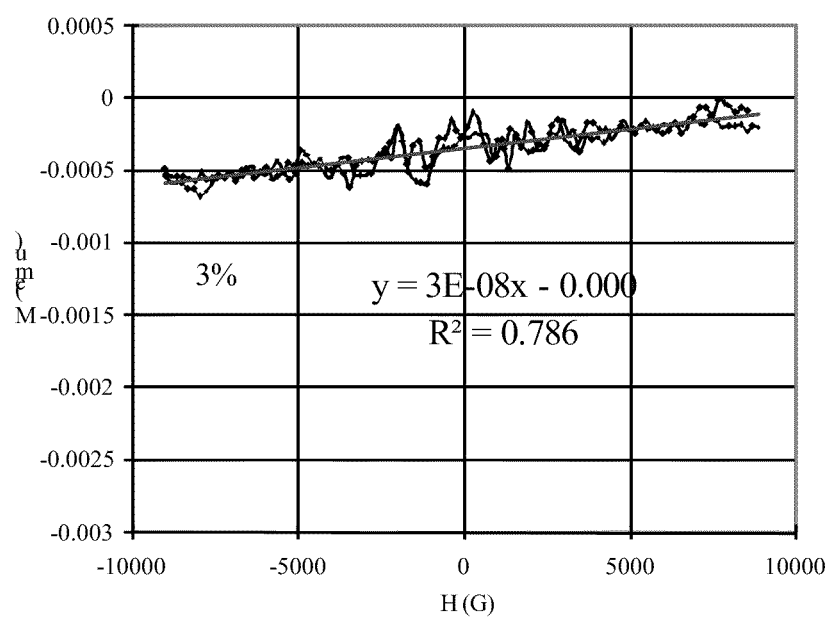
Figure 20C:
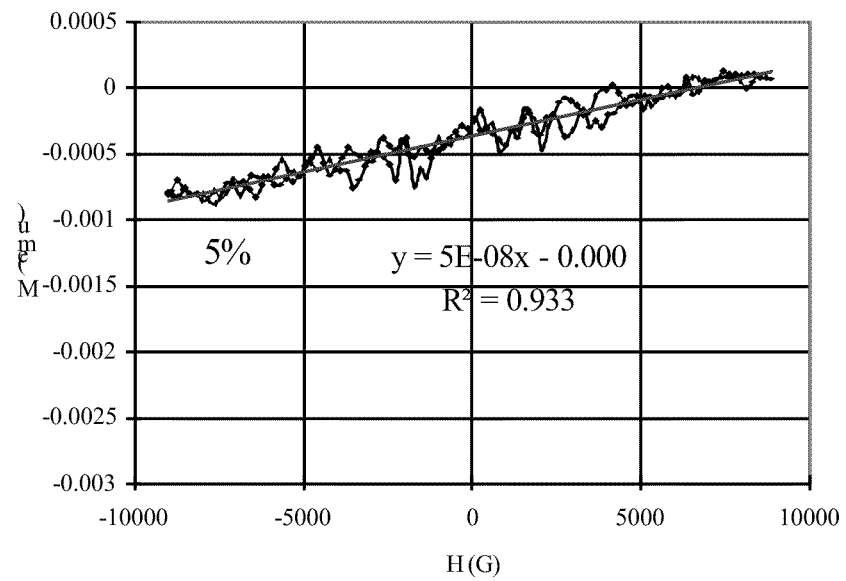
Figure 20D:
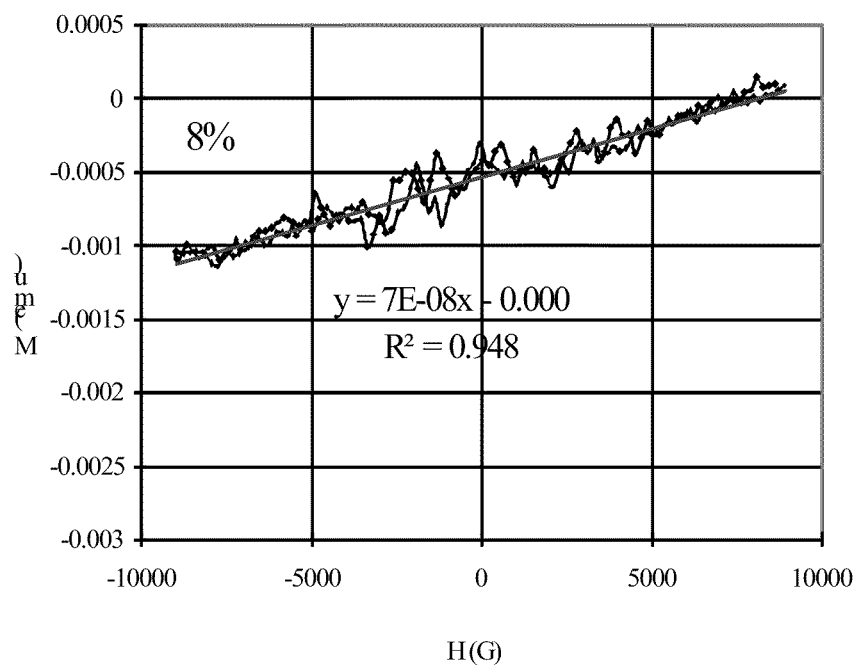
Figure 20E:
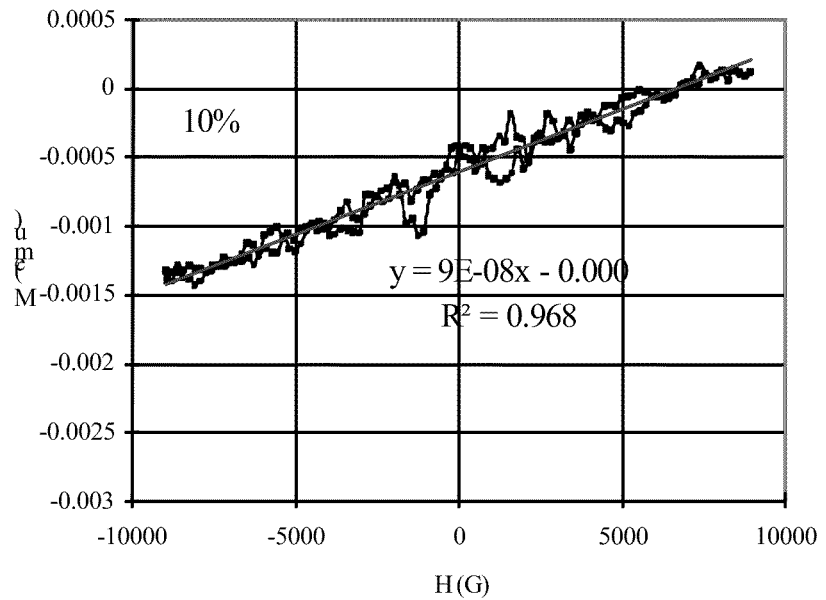

FIG. 19 shows the pH value of aqua solution of various contrast agents with concentrations from 0.3 to 10%. The value of pH varied from 2.6 to 6.5.

FIG. 20a-20d show the magnetic properties of various aqua solutions of Co/glycine with concentration 1, 3, 5, 8 and 10%. An increasing the concentration of Co-based compound increased the paramagnetic behaviour.

The table below summarizes the basic properties of Co-based contrast agents.

| Contrast agent solutions, % | Magnetic properties | Viscosity, cP | Surface tension, dynes/cm | pH | Partition Coefficient, Log P |
|---|---|---|---|---|---|
| 0.5 | paramagnetic | 1.0 | 72.8 | 6.1 | (−0.15) − |
| 5 | paramagnetic | 1.1 | 73.6 | 3.2 | (−0.09) |

Encapsulated Contrast Agent Marker (ECAM)/Constrast Marker Fabrication

Figure 21A:
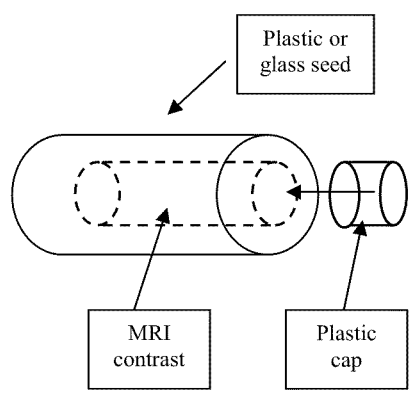
FIG. 21a depicts a schematic diagram of an Encapsulated Contrast Agent Marker (ECAM), also referred to sometimes as a "contrast marker."
Figure 21B:
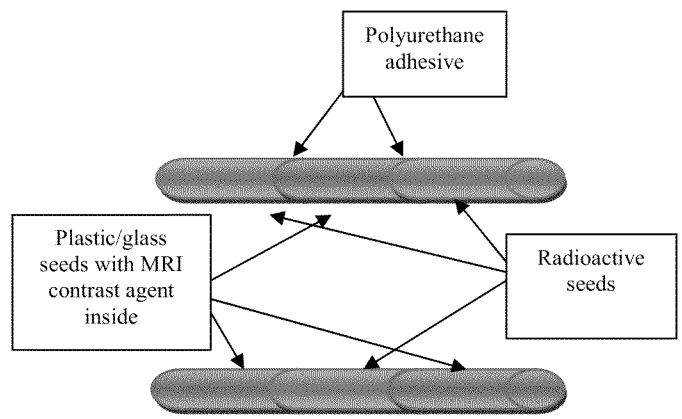
FIG. 21b depicts a schematic diagram of an assembled strand with ECAM and titanium seeds.
Figure 21C:
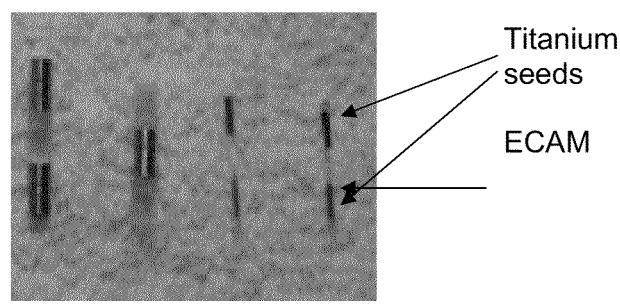
FIG. 21c shows a photograph of assembled brachytherapy strand with ECAMs and titanium seeds.

The Co-based solutions were filtrated through a micro-membrane filter to remove any impurities and injected into the custom design glass capillary tube (FIG. 21a) with the volume of contrast agent of 0.3-2 μL, respectively. Several combinations of glass seeds containing contrast agent were assembled with titanium seeds by using high-strength water-proof polyurethane based adhesive. FIG. 21b shows schematic diagram of assembled strand with ECAM and titanium seeds.

MR Imaging of the Cobalt Complex at Low and High magnetic Fields

MRI served two roles. First, the cobalt complex (C4) was imaged quantitatively in order to establish relaxation parameters which facilitate quantitative simulation, protocol optimization and the ability to compare the complex with other relaxation agents. The second role was qualitative visualization of the complex in seed or strand prototypes.

Quantitative Analysis of the C4 Complex

MR imaging measurements were performed on a 1.5 T clinical scanner (Excite HD, GEHT, Waukesha, Wis.) to characterize the relaxation properties of the new cobalt complex after each new modification of the C4 chemistry was made. Several iterations were performed before obtaining a stable sample. Additional measurements at 3.0 T (Excite HD, GEHT, Waukesha, Wis.) were made once the design of the C4 complex was stable. Each session or iteration (n=5) took approximately 2 hours to collect all the relaxation data.

Concentrations of the complex were prepared in 0.1%, 0.3%, 0.5%, 0.75% and 1.0% solutions provided by the UH group. Theses solutions were placed in a water bath and imaged at room temperature (23° C.). Experiments were performed to ascertain the spin-lattice relaxivity (R1), spin-spin relaxivity (R2) and true spin-spin relaxivity (R2*) at 1.5 T and 3 T using a volume knee coil to excite and receive the MR signal.

R1 measurements were performed using a spin-echo inversion recovery (SE-IR) sequence with parameters: Inversion Time (TI)={0.05, 0.1, 0.2, 0.3, 0.4, 0.5, 0.6, 0.7, 0.8, 0.9, 1.0, 1.2, 1.4, 1.6, 1.8, 2.0} sec, Pulse Repetition Time (TR)=5000, Time to Echo (TE)=10 ms, slice thickness=3 mm, acquisition matrix=256 (frequency)×128 (phase), receiver bandwidth (rBW)=±15 kHz and the number of excitations (NEX)=1.

R2 measurements were carried out using an SE sequence with parameters: TE={15, 20, 40, 60, 100, 150, 200, 250, 300 and 500 ms}, TR=5000 ms, slice thickness=3 mm, matrix size=256×128, rBW=±15 kHz and NEX=1.

R2* measurements were carried out using a multi-echo fast gradient recalled echo (fGRE) sequence with parameters: TR=600 ms, TE varied from 2.2 to 5.7 ms with an echo spacing of 3.3 ms (16 echoes), slice thickness=3 mm, matrix size=256×128, rBW=±15 kHz and NEX=1.

Figure 22:
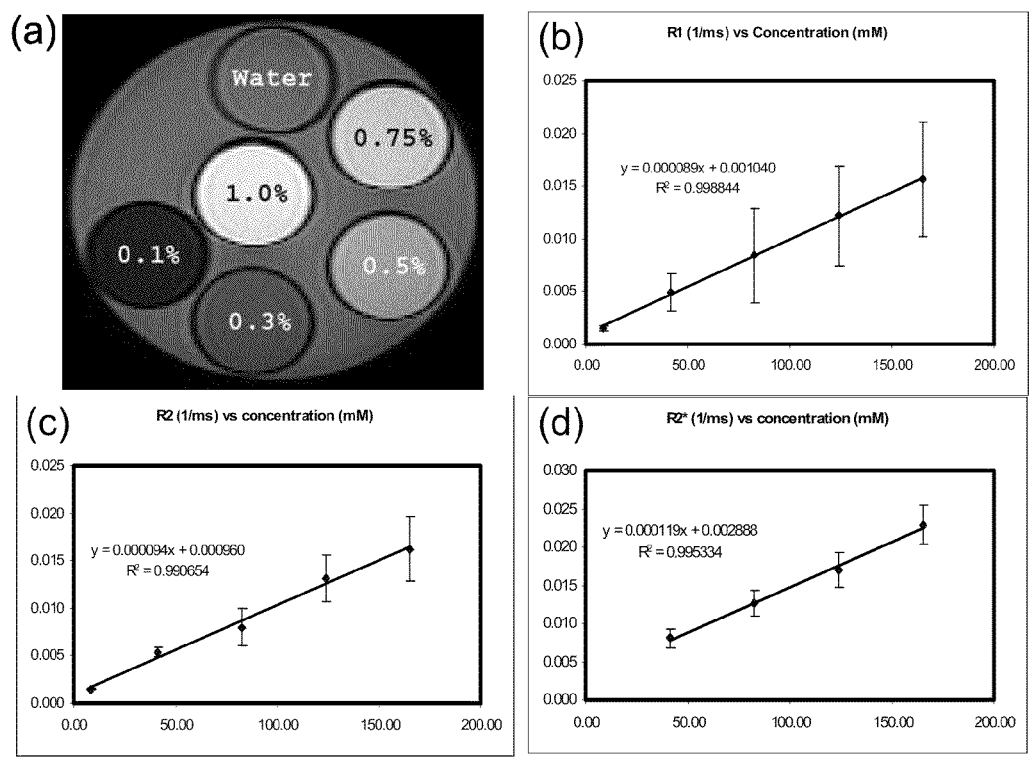
FIGS. 22a-22d depicts the linearity of R1, R2, R2* as a function of the concentration of the C4 complex, also referred to herein as "C4."

FIG. 22a shows the arrangement of the different concentrations of cobalt complex in a water phantom. Relaxation times were inverted to obtain R1, R2 and R2* measurements.

These measurements displayed a linear relationship with cobalt concentration as expected (FIGS. 22b-22d).

Figure 23:
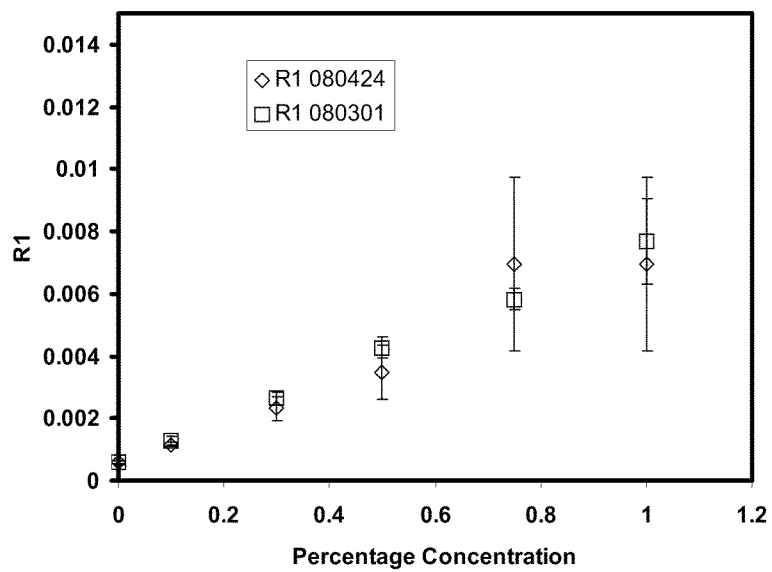
FIG. 23 shows the temporal stability of the T1 response of the C4 complex.

FIG. 23 shows the results of two R1 measurements of the cobalt complex taken 54 days apart. The idea was to see if there was any degradation or breakdown in the complex over time however no statistically significant difference was observed.

The slopes of R1 and R2 curve versus concentration were used to determine the relaxivity (r1 and r2) in $mM^{-1} s^{-1}$ as shown in the following tables. A weighted least-linear squares fitting routine was written in MATLAB to calculate the fit parameters accounting for the uncertainty as well as calculating the net uncertainty in the derived measurement. Note that in the final quantitative analysis, R2* measurements are excluded since the samples seemed to have interfering magnetic effects that could alter results.

TABLE 1

Measured relaxation times (T1, T2) of C4 complex at 1.5T (a) and 3.0T (b)

| | Concentration | | T1 (ms) | | T2 (ms) | |
|---|---|---|---|---|---|---|
| | % Wt | mM | μ | σ | μ | σ |
| (a) | 0.10 | 8.25 | 782.0 | 72.0 | 836.0 | 140.0 |
| | 0.30 | 24.76 | 379.0 | 29.0 | 354.0 | 136.0 |
| | 0.50 | 41.27 | 235.0 | 19.0 | 215.0 | 78.0 |
| | 0.75 | 61.90 | 172.0 | 10.0 | 153.0 | 29.0 |
| | 1.00 | 82.53 | 130.0 | 23.0 | 120.0 | 12.0 |
| (b) | 0.10 | 8.25 | 866.0 | 28.0 | 530.0 | 29.0 |
| | 0.30 | 24.76 | 432.0 | 29.0 | 215.0 | 34.0 |
| | 0.50 | 41.27 | 288.0 | 51.0 | 124.0 | 29.0 |
| | 0.75 | 61.90 | 202.0 | 73.0 | 104.0 | 6.0 |
| | 1.00 | 82.53 | 164.0 | 73.0 | 105.0 | 2.0 |

TABLE 2

Measured relaxivity (r1, r2) of C4 complex at 1.5T (a) and 3.0T (b)

| | | Slope ($mM^{-1} s^{-1}$) | | Intercept $s^{-1}$ | | Corr. |
|---|---|---|---|---|---|---|
| | | μ | σ | μ | σ | Coeff. |
| (a) | r1 | 0.086 | 0.006 | 0.570 | 0.141 | 0.9987 |
| | r2 | 0.097 | 0.010 | 0.404 | 0.238 | 0.9995 |
| | r2/r1 | 1.132 | 0.141 | | | |
| (b) | r1 | 0.070 | 0.008 | 0.572 | 0.084 | 0.9999 |
| | r2 | 0.105 | 0.003 | 1.066 | 0.116 | 0.9869 |
| | r2/r1 | 1.494 | 0.179 | | | |

The relaxivities at 1.5 T were r1=0.086±0.006 $(mM*s)^{-1}$ and r2=0.097±0.010 $(mM*s)^{-1}$. For reference (De Bazelaire C M J, et al, Radiology, 2004), the relaxivities of Gd-DTPA at 1.5 T (23° C.) are r1=4.68±0.06 $(mM*s)^{-1}$ and r2=5.57±0.07 $(mM*s)^{-1}$ corresponding to an r2/r1=1.12±0.01 (similar to the C4 complex response in Table 2). The similarity of the ratios indicates that the T2 effects on signal enhancement are similar. The discrepancy between relaxivities indicates that a higher concentration of C4 is required to effect the same signal enhancement. It is noted that in these measurements, r1 sensitivity decreases at 3.0 T while r2 sensitivity does not appear to, leading to the potential that T2 effects may need to be accounted for in protocols at 3 T (this trend in r1 was observed in the initial measurements seen at 7 T measured by Jim Bankson as well). Obviously, as shown in the data above and the following phantom images of the C4 complex, these concentrations are easily achievable using sealed sources.

Knowing the relaxivities, simulation of the contrast against glandular prostate tissue for T1-weighted and T2-weighted sequences commonly used in the clinic. Note the T1 enhancement in the figure below starts to decrease around 0.75% concentration due to T2 effects on the signal.

Qualitative Visualization of the C4 Complex Using MRI

Prototypes and test vessels containing the C4 complex and various reference markers (such as Gd-DTPA) were imaged as they became available. One of the earliest experiments is shown in the figure below, where the C4 enhancement is shown in agar phantom and in an ex vivo sample of canine prostate using 3D FGRE and 3D FIESTA (a T2-like weighting).

Figure 24:
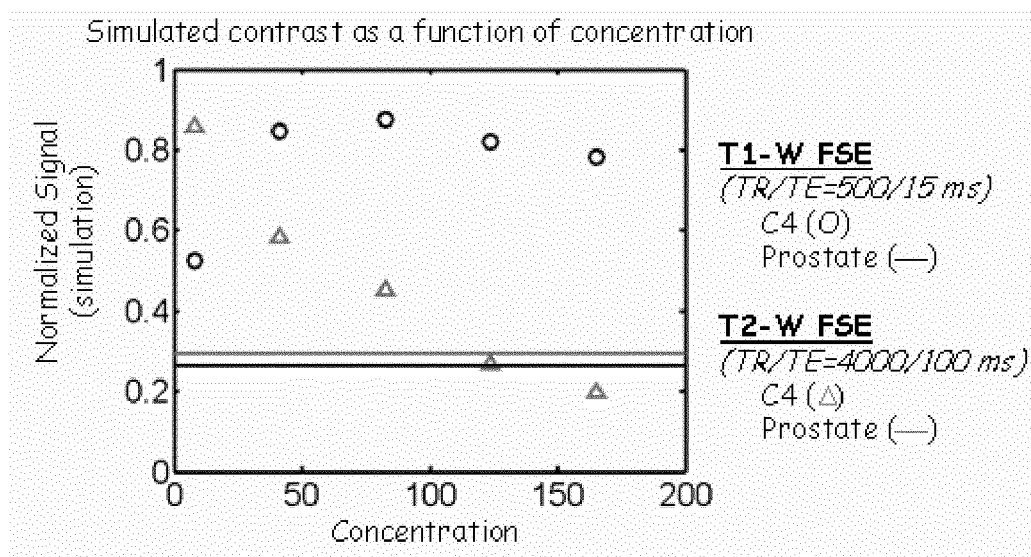
FIG. 24 depicts simulated signal versus concentration for T1 and T2 weighted clinical sequences showing the relative difference between C4 and prostate tissue.
Figure 25:
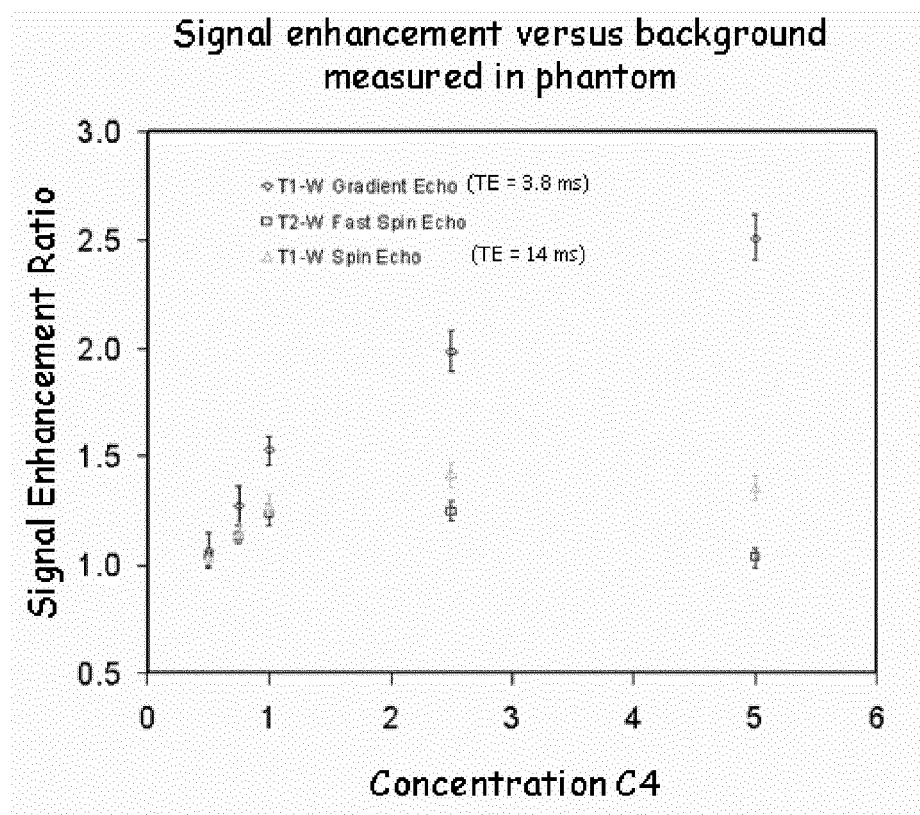
FIG. 25 shows the effect of T2 signal losses at higher TE values simulated in FIG. 24 is measured directly in phantom showing how the contrast changes as a function of concentration.
Figure 26A:
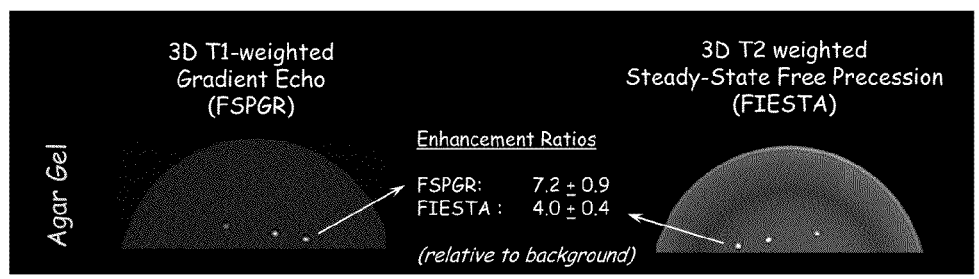
FIGS. 26a and 26b show samples of the contrast agent, C4 in phantom using high resolution 3D T1-weighted fGRE and T2-weighted FIESTA sequences.
Figure 26B:
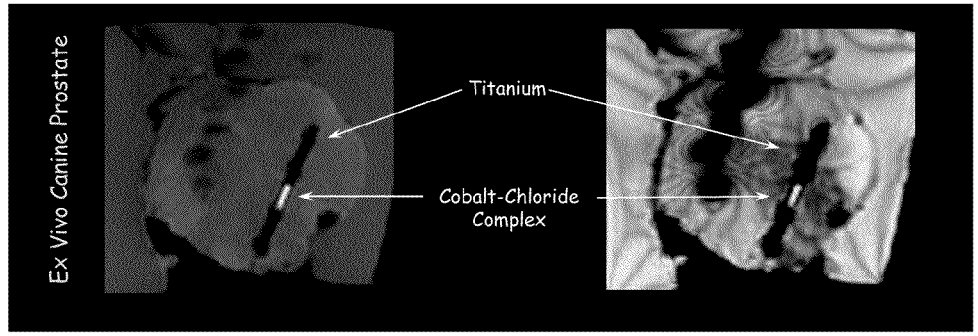

The qualitative imaging sessions have been through many iterations of prototype devices in order to evaluate the vessel effects (content and size) as well as to compare the C4 to gadolinium. Several samples of 0.5 mm and 0.35 mm diameter were prepared with cobalt concentrations ranging from 0.3% to 0.75% (see FIG. 24) were created and placed in rows at a single level inside an agar phantom. Some of these samples contained titanium spacers which divide up the segments where the cobalt complex is kept. The phantoms containing these samples along with control samples containing the same concentrations of gadolinium or distilled water were subjected to several high-resolution 3D FSE, SPGR and FIESTA scans. These scans can be arbitrarily reformatted to any plane in order to visualize the markers. Currently we are still in the process of evaluating different markers prototypes given to us.

Figure 27:
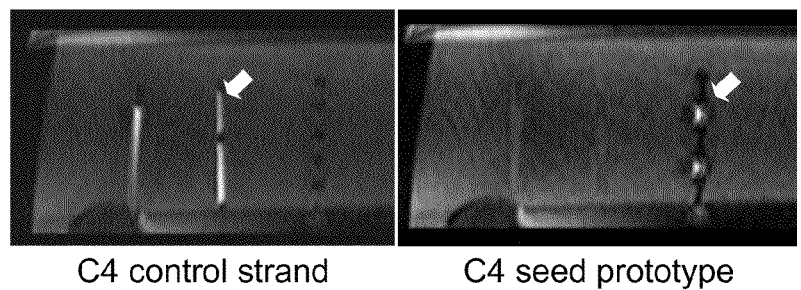
FIG. 27 shows images of prototypical strands containing C4 versus control levels of C4 (0.5% concentration) in phantom using 3D T1-weighted FSPGR imaging at 1.5 T.

FIG. 27 shows SPGR scans containing the both the cobalt complex and gadolinium phantoms. Cobalt is shown in the second of the images.

Qualitative imaging experiments show that the casing containing the contrast agent greatly impacts our ability to see it. It is exceedingly hard to deconvolve these results from instances where the integrity of the vessel was compromised prior to imaging leaving us with reduced quantities of contrast agent to image. When the casing does not interfere with imaging, the response of the C4 complex appears to be as anticipated by the quantitative measurements.

Gd Contrast Markers

Two types of Gd-filled contrast markers 10 were created and evaluated: low-molecular-weight Gd-chelate Magnevist (DTPA-GD) and a high-molecular weight polymeric Gd-chelate. Magnevist is used routinely in the clinic. Its relaxivity is 4.1 mM$^{-1}$s$^{-1}$ at 1.5 T in phosphate-buffered saline. Unger, E. C. S. D., et al., *Gadolinium-Containing Copolymeric Chelates—A New Potential MR Contrast Agent*. MAGMA, 1999, 8(3):154-62. High-molecular-weight polymeric Gd chelates generally have increased rotational correlation time, and hence, increased relaxivity per gadolinium atom. Applicant has synthesized and characterized Gd-chelated polymeric MRI contrast agent 20 based on biodegradable, biocompatible poly(L-glutamic acid) (L-PG) backbone. Wen, X., et al., *Synthesis and Characterization of Poly(L-Glutamic Acid) Gadolinium Chelate: A New Biodegradable MRI Contrast Agent*, Bioconjugate Chemistry, 2004, 15(6):1408-15. To prepare the prototype contrast marker 10 containing L-PG-Bz-DTPA-Gd, one can crosslink L-PG-Bz-DTPA-Gd solution in situ to generate a hydrogel in a capsule. This can be achieved by mixing aqueous solution of L-PG-Bz-DTPA-Gd with a difunctional crosslinker such as hexane diamine and a water soluble carbodiimide as a coupling agent. Previous experiments have shown that L-PG-Bz-DTPA-Gd could readily form hydrogel in the presence of a crosslinker. The crosslink density can be varied by varying the molar ratio of L-PG-Bz-DTPA-Gd to the crosslinker.

Figure 3A:
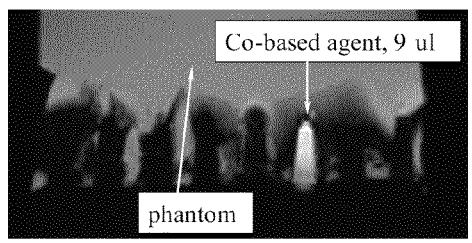
FIG. 3a shows a Co-based contrast agent that has positive contrast in a 1.5-T MRI.
Figure 3B:
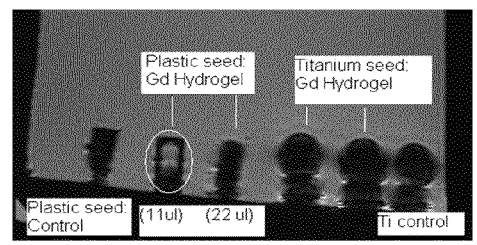
FIG. 3b shows a Gd Hydrogel contrast agent that has a positive contrast in a 1.5-T MRI.

A Gd-chelated polymeric MRI contrast agent 20 (Gd Hydrogel) based on a biodegradable, biocompatible poly(L-glutamic acid) (L-PG) backbone was also synthesized and characterized. The resulting polymer, L-PG-Bz-DTPA-Gd, synthesized directly from L-PG and monofunctional p-aminobenzyl-DTPA(acetic acid-t-butyl ester), exhibited T$_1$ relaxivity of 25 mM$^{-1}$s$^{-1}$ at 1.5 T, which was more than 6 times greater than that of Gd-DTPA. FIG. 3b illustrates the positive contrast at low concentrations in a polymer casing 15, but negative contrast at higher concentrations due to T2* effects. "Blooming" occurs with MR imaging when the contrast agent 20 is encapsulated by titanium and cannot be visualized due to the susceptibility artifacts To characterize the contrast agents 20, they were filtrated and injected into the glass capillary tube with 4 mm in length and OD=0.8 mm, ID=0.5 mm with volume of 0.5-1 µL. Water-proton relaxivities were measured at variable temperature (278-335 K), and as a function of magnetic field (1.5 T, 3 T, 4.7 T, and 7 T). Slight differences between the relaxivities of these agents at different field strengths will require slightly different concentrations for optimal visibility at these field strengths. By pH dependency of the proton relaxivities we will evaluate the synthesized CAM for pH-responsive MRI contrast agent 20 applications. Although 4.7 T is not a field strength commonly associated with clinical MRI, it complements the data collected at more clinically relevant field strengths and helps to identify trends in agent relaxivity.

Figure 4A:
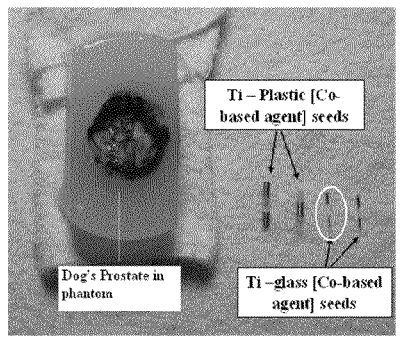
FIG. 4a shows a canine prostate in phantom with titanium seeds within a titanium seed-glass [Co-based agent]-titanium seed strand.

Acrylic and glass hollow contrast markers 10 containing 2-5 µL of the $(CoCl_2)_{0.8}(C_2H_5NO_2)_{0.2}$ aqueous solution (10-1 wt. %) were well visualized with a relative signal intensity ranging from 10751 to 32767 in a phantom under 1.5-T MRI (T$_1$). The various combinations of [plastic/glass]-titanium-[plastic/glass] and titanium-[plastic/glass]-titanium rows of therapy seeds 35 were visualized in a dog prostate, and calculations verified the distance to the center of the titanium therapy seeds 35 (FIG. 4). Both novel and FDA approved Gd-based agents are shown herein as successfully incorporated inside and around polymers such as PEEK and PMMA to achieve high positive contrast signals Likewise, C4 contrast agent and FDA approved Gd-based agents have been incorporated both inside and around polymers and achieved high positive contrast signals.

Characterization of the C4 Complex at 7 T

Methods

Samples of the cobalt complex with concentrations of 0 mM, 8.25 mM, 24.76 mM, 41.27 mM, 61.9 mM, and 85.23 mM were transferred into NMR sample tubes, immersed in relaxed water, and scanned at 7 T using a Biospec USR30/70 small animal NMR/MRI system. Characteristic T1, T2, and T2* relaxation times of the preparations were measured at each concentration. T1 measurements were made using a fast spin-echo saturation-recovery sequence (TE=63 ms; TR=400 ms, 500 ms, 1000 ms, 1500 ms, 2500 ms, 500 ms; FOV=3.2 cm×3.2 cm; matrix=64×64; echo train length=12; slice thickness=1 mm). T2 measurements were made using a CPMG multi-spin-echo sequence (TE=n×15 ms, 1≤n≤24; TR=1100 ms). T2* measurements were made using a multi-gradient echo sequence (TE=1.5 ms+n×3.25 ns, 0≤n≤15; TR=500 ms, 4000 ms). The image matrix and slice prescription for all measurements were kept constant. The characteristic T1, T2, and T2* relaxation time constants of each compartment were measured using Paravision 4.0, and the relaxivities of the contrast agent were estimated by fitting measured data to the Solomon-Bloembergen-Morgan model using Matlab.

Results

Figure 28:
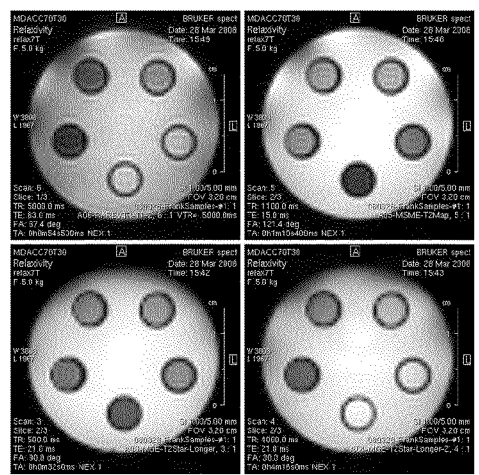
FIG. 28 shows representative images from saturation-recovery sequence (upper left), CPMG multi-spin-echo sequence (upper right), and multi-gradient echo sequence (bottom images) with different T1-weightings.
Figure 29:
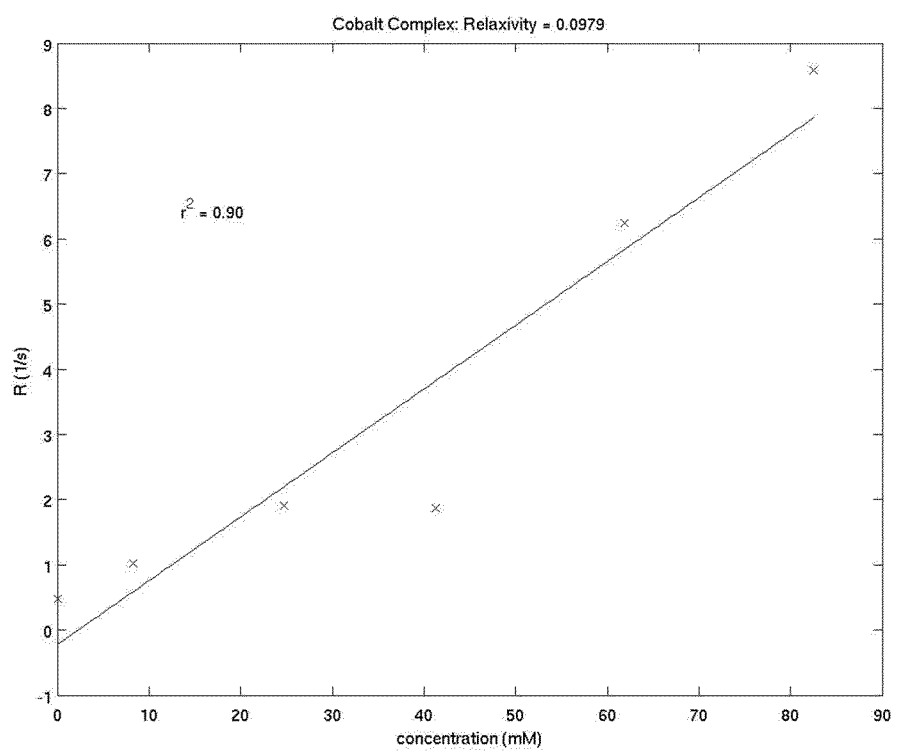
FIG. 29 depicts regression of data to relaxation model. The relaxivity of the agent is equal to the slope of the line.

Representative images can be seen in FIG. 28, where the least concentrated preparation is in the compartment closest to the bottom of the image, and concentrations increase in a counterclockwise fashion. Linear regression of T1 measurements to the relaxation model can be seen in FIG. 29, while Table 1 lists the characteristic relaxation times measured for each sample, along with the T1, T2, and T2* relaxivity estimates. The T1 relaxivity of the cobalt complex was measured to be 0.0979 $(mM \cdot s)^{-1}$, while its T2 and T2* relaxivities were measured to be 0.502 $(mM \cdot s)^{-1}$ and ~0.618 $(mM \cdot s)^{-1}$, respectively. For reference, the T1 relaxivity of Magnevist is approximately 5.3 $(mM \cdot s)^{-1}$ at 7 T. Magnevist is a FDA-approved T1-reducing MRI contrast agent that is widely used in clinical practice.

The ability of a T1-reducing contrast agent to generate a very bright signal against a background of normal tissue is a function of the relaxivity and concentration of the contrast agent, the characteristic relaxation time constants of background tissues, and the acquisition parameters of the MR imaging sequence. The same contrast between encapsulated markers and surrounding tissue can be achieved using the cobalt complex or clinically available agents such as Magnevist, but because the relaxivity of the cobalt complex is lower, a higher concentration will be required. A concentration-dependent chemical shift was observed in cobalt complex samples that may cause varying degrees of image misregistration, depending on the concentration of the agent and on the acquisition parameters of the MR imaging sequence.

TABLE 3

| Concentration (mM) | T2 | T1 | T2* | T2*-2 | |
|---|---|---|---|---|---|
| 0 | 120.85 | 2118.485 | 120.89 | 388.77 | |
| 8.25 | 74.85 | 980.805 | 141.415 | 146.68 | |
| 24.76 | 45.175 | 524.66 | 50.42 | 52.755 | |
| 41.27 | 31.14 | 533.955 | 32.37 | 34.135 | |
| 61.9 | 22.96 | 160.45 | 24.85 | 25.55 | |
| 82.53 | 20.84 | 116.5 | 17.99 | 17.64 | |
| | R2 = 0.5023 | R1 = 0.0979 | R2* = 0.5939 | R2* = 0.6429 | R2/R1 = 5.13 |
| | Rsquare = 0.9831 | Rsquare = 0.9027 | Rsquare = 0.9865 | Rsquare = 0.9944 | |

Contrast agents have been traditionally characterized by their relaxivities. The model that defines the relaxivities (slope of linear regression curve) is the Solomon-Bloembergen-Morgan model. This model gives the formula y=mx+b, and the relaxivity is defined as 'm' or the slope of the curve. The y axis is R (1/T) and the x axis is concentration. In other words, the y axis is 'R' defined as the relaxation rate $(ms^{-1})$ which is the inverse of 'T' which is the relaxation time (ms). The C4 relaxivities (r1 and r2) were determined, and the relaxivity ratios were calculated at 1.5 T, 3 T, and 7 T (1.132, 1.494, 5.13, respectively The C4 relaxivity ratios were very similar to Gd relaxivity ratios (1.5 T=1.12, and 7 T=5.13) So, using the Gd model y=mx+b, the concentration range of Gd was optimized.

Therefore, a certain concentration range for C4 that had positive contrast. This range in concentration for Cobalt was 0.1%-8.25 mM which corresponds to a T1 relaxation time of 782 ms, and 10%-825 mM which corresponds to a T1 relaxation time of 61 ms. By taking the concentrations which are consistent with similar relaxation times (T1) or relaxation rates (R1=1/T1) for Gd or any other contrast agents, we can use this methodology to calculate concentrations that provide similar signal intensity.

EXAMPLES

The following examples are related to the novel contrast agent C4.

Example 1

This example serves to illustrate fabrication of novel MRI visible marker by using biocompatible Poly(methyl methacrylate), (PMMA) and contrast agent C4.

The C4 water solution with concentration of 0.75% was filtrated through a micro-membrane filter to remove any impurities and injected into the PMMA capillary closed with one side. The dimensions of capillary are: outside diameter, (OD)=0.8 mm, inside diameter, (ID)=0.3 mm and length, (l)=3 mm. The PMMA tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal (see FIG. 34).

Example 2

This example serves to illustrate fabrication of novel MRI visible marker by using biocompatible Poly(methyl methacrylate), (PMMA) and contrast agent C4.

The C4 water solution with concentration of 0.3% was filtrated through a micro-membrane filter to remove any impurities and injected into the PMMA capillary closed with one side. The dimensions of capillary are: outside diameter, (OD)=0.8 mm, inside diameter, (ID)=0.6 mm and length, (l)=4 mm. The PMMA tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 3

This example serves to illustrate fabrication of novel MRI visible marker by using biocompatible Polyetheretherketon, (PEEK) and contrast agent C4.

The C4 water solution with concentration of 0.75% was filtrated through a micro-membrane filter to remove any impurities and injected into the PEEK capillary closed with one side. The dimensions of capillary are: outside diameter, (OD)=0.8 mm, inside diameter, (ID)=0.6 mm and length, (l)=3 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows good positive MRI signal.

Example 4

This example serves to illustrate fabrication of novel MRI visible marker by using glass and contrast agent C4.

The C4 water solution with concentration of 0.15% was filtrated through a micro-membrane filter to remove any impurities and injected into the glass capillary closed with one side. The dimensions of capillary are: outside diameter, (OD)=0.8 mm, inside diameter, (ID)=0.6 mm and length, (l)=3 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 5

This example serves to illustrate fabrication of novel MRI visible marker by using biocompatible Poly(methyl methacrylate), (PMMA) and contrast agent C4.

The C4 water solution with concentration of 0.5% was filtrated through a micro-membrane filter to remove any impurities and injected into the PMMA capillary closed with one side. The dimensions of capillary are: outside diameter, (OD)=0.8 mm, inside diameter, (ID)=0.6 mm and length, (l)=4.5 mm. The PMMA tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 6

This example serves to illustrate fabrication of novel MRI visible marker by using biocompatible Polyetheretherketon, (PEEK) and contrast agent C4.

The C4 water solution with concentration of 0.5% was filtrated through a micro-membrane filter to remove any impurities and injected into the PEEK capillary closed with one side. The dimensions of capillary are: outside diameter, (OD)=0.8 mm, inside diameter, (ID)=0.6 mm and length, (l)=4.5 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 7

This example serves to illustrate fabrication of novel MRI visible marker by using biocompatible Polyetheretherketon, (PEEK) and contrast agent Magnevist.

Magnevist was diluted in water with ratio 1/20 and filtrated through a micro-membrane filter to remove any impurities and injected into the PEEK capillary closed with one side. The dimensions of capillary are: outside diameter, (OD)=0.8 mm, inside diameter, (ID)=0.6 mm and length, (l)=4.5 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 8

This example serves to illustrate fabrication of novel MRI visible marker by using biocompatible Poly(methyl methacrylate), (PMMA) and contrast agent Magnevist.

Magnevist was diluted in water with ratio 1/20 and filtrated through a micro-membrane filter to remove any impurities and injected into the PMMA capillary closed with one side. The dimensions of capillary are: outside diameter, (OD)=0.8 mm, inside diameter, (ID)=0.6 mm and length, (l)=4.5 mm. The PMMA tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 9

This example serves to illustrate fabrication of novel MRI visible marker by using Polytetrafluoroethylene, (PTFE) or Teflon and contrast agent C4.

The C4 water solution with concentration of 1.0% was filtrated through a micro-membrane filter to remove any impurities and injected into the PMMA capillary closed with one side. The dimensions of capillary are: outside diameter, (OD)=0.8 mm, inside diameter, (ID)=0.6 mm and length, (l)=4.5 mm. The PTFE tap was fastened to the capillary end to prevent leakage of the contrast agent. Fabricated marker was placed inside the agarose phantom and tested by clinical 1.5 T MRI. The result shows excellent positive MRI signal.

Example 10

This example serves to illustrate fabrication of novel MRI visible marker by using biocompatible Poly(methyl methacrylate), (PMMA) and contrast agent OptiMark.

OptiMark was diluted in water with ratio 1/20 and filtrated through a micro-membrane filter to remove any impurities and injected into the PMMA capillary closed with one side. The dimensions of capillary are: outside diameter, (OD)=0.8 mm, inside diameter, (ID)=0.6 mm and length, (l)=4.5 mm. The PMMA tap was fastened to the capillary end and locally heated by laser beam to secure the conjunction and to prevent leakage of the contrast agent. Fabricated marker was placed inside the agarose phantom and tested by clinical 1.5 T MRI. The result shows good positive MRI signal.

Example 11

This example serves to illustrate fabrication of novel MRI visible marker by using biocompatible Polyetheretherketon, (PEEK) and contrast agent ProHance.

ProHance was diluted in water with ratio 1/20 and filtrated through a micro-membrane filter to remove any impurities and injected into the PEEK capillary closed with one side. The dimensions of capillary are: outside diameter, (OD)=0.8 mm, inside diameter, (ID)=0.6 mm and length, (l)=5.5 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows good positive MRI signal.

Example 12

This example serves to illustrate fabrication of novel MRI visible marker by using biocompatible Polyetheretherketon, (PEEK) and contrast agent MultiHance.

MultiHance was diluted in water with ratio 1/20 and filtrated through a micro-membrane filter to remove any impurities and injected into the PEEK capillary closed with one side. The dimensions of capillary are: outside diameter, (OD)= 0.8 mm, inside diameter, (ID)=0.6 mm and length, (l)=5.5 mm. The PEEK tap was fastened to the capillary end and locally heated by laser beam to secure the conjunction and to prevent leakage of the contrast agent. Fabricated marker was placed inside the agarose phantom and tested by clinical 1.5 T MRI. The result shows good positive MRI signal.

Example 13

This example serves to illustrate fabrication of novel MRI visible marker by using biocompatible grade Polypropylene and contrast agent C4.

The C4 water solution with concentration of 0.3% was filtrated through a micro-membrane filter to remove any impurities and injected into the polypropylene capillary closed with one side. The dimensions of capillary are: outside diameter, (OD)=0.8 mm, inside diameter, (ID)=0.6 mm and length, (l)=4.5 mm. The polypropylene tap was fastened to the capillary end to prevent leakage of the contrast agent. Fabricated marker was placed inside the agarose phantom and tested by clinical 1.5 T MRI. The result shows excellent positive MRI signal.

Example 14

This example serves to illustrate fabrication of novel MRI visible marker by using biocompatible Polyethylene and contrast agent Magnevist.

Magnevist was diluted in water with ratio 1/20 and filtrated through a micro-membrane filter to remove any impurities and injected into the Polyethylene capillary closed with one side. The dimensions of capillary are: outside diameter, (OD)= 0.8 mm, inside diameter, (ID)=0.6 mm and length, (l)=4.5 mm. The Polyethylene tap was fastened to the capillary end and locally heated by laser beam to secure the conjunction and to prevent leakage of the contrast agent. Fabricated marker was placed inside the agarose phantom and tested by clinical 1.5 T MRI. The result shows excellent positive MRI signal.

Example 15

This example serves to illustrate fabrication of novel MRI visible marker by using biocompatible grade Polyamides and contrast agent C4.

The C4 water solution with concentration of 0.3% was filtrated through a micro-membrane filter to remove any impurities and injected into the Polyamides capillary closed with one side. The dimensions of capillary are: outside diameter, (OD)=0.7 mm, inside diameter, (ID)=0.5 mm and length, (l)=4 mm. The Polyamides tap was fastened to the capillary end to prevent leakage of the contrast agent. Fabricated marker was placed inside the agarose phantom and tested by clinical 1.5 T MRI. The result shows excellent positive MRI signal.

Example 16

This example serves to illustrate fabrication of novel MRI visible marker by using biocompatible grade Polyester and contrast agent C4.

The C4 water solution with concentration of 0.75% was filtrated through a micro-membrane filter to remove any impurities and injected into the Polyester capillary closed with one side. The dimensions of capillary are: outside diameter, (OD)=0.8 mm, inside diameter, (ID)=0.3 mm and length, (l)=3 mm. The Polyester tap was fastened to the capillary end to prevent leakage of the contrast agent. Fabricated marker was placed inside the agarose phantom and tested by clinical 1.5 T MRI. The result shows excellent positive MRI signal.

Example 17

This example serves to illustrate fabrication of novel MRI visible marker by using biocompatible grade Polyurethanes and contrast agent C4.

The C4 water solution with concentration of 0.5% was filtrated through a micro-membrane filter to remove any impurities and injected into the Polyurethanes capillary closed with one side. The dimensions of capillary are: outside diameter, (OD)=0.8 mm, inside diameter, (ID)=0.3 mm and length, (l)=4.5 mm. The Polyurethanes tap was fastened to the capillary end to prevent leakage of the contrast agent. Fabricated marker was placed inside the agarose phantom and tested by clinical 1.5 T MRI. The result shows excellent positive MRI signal.

Example 18

This example serves to illustrate fabrication of novel MRI visible marker by using biocompatible grade Polyvinylchloride and contrast agent C4.

The C4 water solution with concentration of 0.5% was filtrated through a micro-membrane filter to remove any impurities and injected into the Polyvinylchloride capillary closed with one side. The dimensions of capillary are: outside diameter, (OD)=0.7 mm, inside diameter, (ID)=0.5 mm and length, (l)=4 mm. The Polyvinylchloride tap was fastened to the capillary end to prevent leakage of the contrast agent. Fabricated marker was placed inside the agarose phantom and tested by clinical 1.5 T MRI. The result shows excellent positive MRI signal.

Example 19

This example serves to illustrate fabrication of novel MRI visible marker by using biocompatible grade Polyvinylchloride and contrast agent Magnevist.

Magnevist was diluted in water with ratio 1/20 and filtrated through a micro-membrane filter to remove any impurities and injected into the Polyvinylchloride capillary closed with one side. The dimensions of capillary are: outside diameter, (OD)=0.7 mm, inside diameter, (ID)=0.5 mm and length, (l)=4 mm. The Polyvinylchloride tap was fastened to the capillary end to prevent leakage of the contrast agent. Fabricated marker was placed inside the agarose phantom and tested by clinical 1.5 T MRI. The result shows excellent positive MRI signal.

Example 20

This example serves to illustrate fabrication of novel MRI visible marker by using biocompatible grade polyglycolic acid, (PGA) and contrast agent C4.

The C4 water solution with concentration of 0.5% was filtrated through a micro-membrane filter to remove any impurities and injected into the PGA capillary closed with one side. The dimensions of capillary are: outside diameter, (OD)=0.8 mm, inside diameter, (ID)=0.3 mm and length, (l)=3 mm. The PGA tap was fastened to the capillary end to prevent leakage of the contrast agent. Fabricated marker was placed inside the agarose phantom and tested by clinical 1.5 T MRI. The result shows excellent positive MRI signal.

Example 21

This example serves to illustrate fabrication of novel MRI visible marker by using biocompatible grade Poliglycolic acid, (PGA) and contrast agent Magnevist.

Magnevist was diluted in water with ratio 1/20 and filtrated through a micro-membrane filter to remove any impurities and injected into the PGA capillary closed with one side. The dimensions of capillary are: outside diameter, (OD)=0.8 mm, inside diameter, (ID)=0.3 mm and length, (l)=3 mm. The PGA tap was fastened to the capillary end to prevent leakage of the contrast agent. Fabricated marker was placed inside the agarose phantom and tested by clinical 1.5 T MRI. The result shows excellent positive MRI signal.

Summary of the examples for fabrication and testing the MRI visible marker are presented below in Table 4.

TABLE 4

| Examples | Marker Material | Marker size, (mm) OD | ID | Contrast agent | Concentration, % | Amount of Contrast agent, (µl) | MRI Visualization |
|---|---|---|---|---|---|---|---|
| 1 | Poly(methyl methacrylate), (PMMA) | 0.8 | 0.3 | C4 | 0.75 | 0.28 | excellent |
| 2 | PMMA | 0.8 | 0.6 | C4 | 0.3 | 0.84 | excellent |
| 3 | Polyetheretherketon, (PEEK) | 0.8 | 0.3 | C4 | 0.75 | 0.28 | good |
| 4 | Glass | 1.0 | 0.3 | C4 | 0.15 | 0.28 | excellent |
| 5 | PMMA | 0.8 | 0.6 | C4 | 0.5 | 0.9 | excellent |
| 6 | PEEK | 0.8 | 0.6 | C4 | 0.5 | 0.9 | excellent |
| 7 | PEEK | 0.8 | 0.6 | Magnevist | Diluted 1/20 | 0.84 | excellent |
| 8 | PMMA | 0.8 | 0.6 | Magnevist | Diluted 1/20 | 0.84 | excellent |
| 9 | Polytetrafluoroethylene, (PTFE) | 0.8 | 0.6 | C4 | 1.0 | 0.84 | excellent |
| 10 | PMMA | 0.8 | 0.6 | OptiMark | Diluted 1/20 | 0.84 | good |
| 11 | PEEK | 0.8 | 0.6 | ProHance | Diluted 1/20 | 1.13 | good |
| 12 | PEEK | 0.8 | 0.6 | MultiHance | Diluted 1/20 | 1.13 | good |
| 13 | Polypropylene | 0.8 | 0.6 | C4 | 0.3 | 0.84 | excellent |
| 14 | Polyethylene | 0.8 | 0.6 | Magnevist | Diluted 1/20 | 0.84 | excellent |
| 15 | Polyamides | 0.7 | 0.5 | C4 | 0.3 | 0.56 | excellent |
| 16 | Polyester | 0.8 | 0.3 | C4 | 0.75 | 0.28 | excellent |
| 17 | Polyurethanes | 0.8 | 0.6 | C4 | 0.5 | 0.84 | excellent |
| 18 | Polyvinylchloride | 0.7 | 0.5 | C4 | 0.5 | 0.56 | excellent |
| 19 | Polyvinylchloride | 0.7 | 0.5 | Magnevist | Diluted 1/20 | 0.56 | excellent |
| 20 | Polyglycolic acid, (PGA) | 0.8 | 0.3 | C4 | 0.5 | 0.28 | excellent |
| 21 | Polyglycolic acid, (PGA) | 0.8 | 0.3 | Magnevist | Diluted 1/20 | 0.28 | excellent |

Example 22

This example serves to illustrate integration of novel MRI visible marker (fabricated as described in Example 2) next to the titanium seeds by using standard biodegradable (polyglycolic acid) brachytherapy strand. FIG. 6 shows the schematic diagram of a loaded strand with titanium seeds and MRI visible markers. FIG. 35a shows the photograph of the fabricated brachytherapy strand: MRI visible markers were integrated with dummy titanium seeds. FIG. 35b shows that MRI visible markers permit positive MRI identification of titanium seeds in brachytherapy strand.

Example 23

This example serves to illustrate fabrication of novel MRI visible marker by using an absorptive fiber (cotton rope), contrast agent C4 and biocompatible Poly(methyl methacrylate)-(PMMA) polymer dissolved in dichloromethane.

The C4 water solution with concentration of 0.5% was filtrated through a micro-membrane filter to remove any impurities and impregnated into the absorptive fiber. The dimensions of fiber are: outside diameter, (OD)=0.6 mm and length, (l)=20 mm. After saturation of C4 agent into the absorptive fiber, fiber was coated by polymer (25%-PMMA/85%-dichloromethane) solution. The polymer solution was entrapped after the overcoating is dry. The thickness of the coating may be regulated by number of fiber immersion into the polymer solution. In our experiment the final OD of the fiber with polymer coat was 0.8 mm. Fabricated marker was placed inside the agarose phantom and tested by clinical 1.5 T MRI. The result shows good positive MRI signal.

Example 24

This example serves to illustrate fabrication of novel MRI visible marker by using an absorptive fiber (cotton rope), contrast agent Magnevist and biocompatible Poly(methyl methacrylate)-(PMMA) polymer dissolved in dichloromethane.

Magnevist was diluted in water with ratio 1/20 and filtrated through a micro-membrane filter to remove any impurities and impregnated into the absorptive fiber. The dimensions of fiber are: outside diameter, (OD)=0.6 mm and length, (l)=20 mm. After saturation of contrast agent into the absorptive fiber, fiber was coated by polymer (25%-PMMA/85%-dichloromethane) solution. The polymer solution was entrapped after the overcoating is dry. The thickness of the coating may be regulated by number of fiber immersion into the polymer solution. In our experiment the final OD of the fiber with polymer coat was 0.8 mm. Fabricated marker was placed inside the agarose phantom and tested by clinical 1.5 T MRI. The result shows good positive MRI signal. FIG. 36 shows the MRI image of the ECAM fabricated by using absorptive fiber, magnevist and PMMA/dichloromethane solution.

Another Prophetic Example for in vitro Evaluation

Contrast markers 10 can be implanted into a prostate phantom to test the imaging performance of a contrast marker 10, and optimize MRI-based dosimetric evaluation of the prostate and surrounding critical organ structures in vitro. To test the performance of the contrast marker 10 with respect to facilitating MRI-based dosimetric evaluation of a tumor-bearing canine prostate and critical organ structures in vivo a pilot study of MRI perfusion, diffusion, and spectroscopy with the contrast marker 10 can be conducted. One can determine, in a large-animal in vivo model of cancer, whether the contrast marker 10 permits the use of functional MRI to enhance the delivery and dosimetric evaluation of prostate brachytherapy.

To test the performance of the contrast marker 10 with respect to facilitating MRI-based dosimetric evaluation of the prostate and critical organ structures in a prostate, the strand 30 containing non-radioactive titanium seeds (functioning as spacer elements 45) are preloaded along with contrast markers 10 and the strand 30 implanted into the prostate phantom. Optimization of MRI-based dosimetry of the prostate and surrounding critical organ structures can be performed. Dosimetry can be evaluated using an arbitrary fixed activity and prostate dose prescription for dosimetric calculations.

Figure 7:
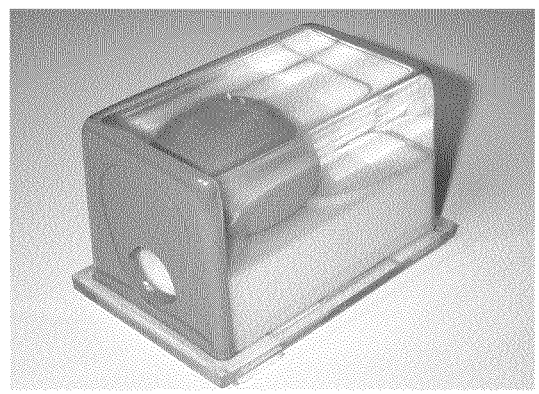
FIG. 7 shows a prostate phantom as a clear acrylic box that houses gels simulating the prostate and other structures.

In order to conduct preliminary testing of the system, one can use a disposable prostate phantom (Model M53F, Computerized Imaging Reference System, Inc., Norfolk, Va.), shown in FIG. 7. The phantom contains a liquid medium surrounding a Zerdine™ water-based polymer gel prostate and a penetrable "perineum" for catheter insertion. Though intended for ultrasound imaging, the phantom components are CT and MR-compatible and are easily visualized on CT and MR images. The positional grid template routinely used in clinical prostate brachytherapy can be affixed to the front of the phantom for positional measurements. The strand 30 containing the non-radioactive seeds (spacer elements 45) with contrast markers 10 will be positioned accurately within this grid at any one of the grid locations.

An ultrasound Endo-PII probe (Model G20, Sonoline, Siemens Medical Systems, Mount View, Calif.) can be inserted into the rectal opening in the phantom and ultrasound images can be captured every 5 mm within the phantom. Images are typically taken from the base to the apex of the prostate. The output screen has an electronic grid superimposed on all the images to simulate the locations of the needle i.e. the strand 30 insertions. These captured images can then be transferred to the prostate brachytherapy treatment planning system Variseed 7.2. (Varian Medical Systems, Charlottesville, Va.). The organ structures within the phantom can be contoured. Multiple treatment-plans can be generated based on various predetermined geometries of the therapy seeds 35. Based on an assumed activity of each therapy seed 35 to be 1 mCi, dose distributions and dose volume histograms (DVH's) can be computed.

Based on the simulated treatment plans, the spacer elements 45 with contrast markers 10 can be physically placed in the phantom at locations determined on a given treatment plan. The phantom can be placed into a standard head coil and inserted into the bore of a 1.5 T and 3 T superconducting MRI scanner (Signa, GE Medical Systems, Waukesha, Wis.). A series of images can be acquired using clinical MRI sequencing protocols. The acquired multiple image sets can be transferred to a Radiation Oncology DICOM storage server Evercore (TeraMedica, Milwaukee, Wis.) from where they can be imported into Variseed 7.2. The prostate and organ structures within the phantom can be contoured from the acquired images. Following the identification of contrast markers 10, the location of the therapy seeds 35 can be determined and dose computed for each treatment plan.

To illustrate the ability to identify therapy seeds 35 using contrast markers 10, non-radioactive seeds (spacer elements 45) without contrast markers 10 can be implanted into a separate prostate phantom. The seeds can be implanted into identical coordinates as the phantom with contrast markers 10. MR imaging data sets of the phantoms with and without contrast markers 10 can then be qualitatively compared.

In order to illustrate the superiority of MR-based dosimetry using contrast markers 10 over CT-based dosimetry, qualitative comparisons between MR- and CT-based dosimetry can be performed. Using a GE multi-slice CT scanner (GE Medical Systems, Pewaukee, Wis.), a CT data set of the identical phantom can be obtained. Following transfer of the CT data sets to Variseed 7.2, the prostate and critical organ structures can be contoured to generate CT-based dosimetry. A qualitative comparison of MR-based dosimetry to CT-based dosimetry can be performed.

Yet Another Prophetic Example for in vivo Evaluation

A total of 4 male mongrel dogs can be used for these studies. Two animals will be implanted with non-radioactive seeds (spacer elements 45) with contrast markers 10 under MR guidance for the purpose of validating the ability to image the seeds and obtain useful treatment planning in an in vivo large animal model using MRI anatomy. The other two animals will have transmissible venereal tumor (TVT) inoculated into the prostate using sterile techniques (TVT source: fresh or frozen tissue harvested from SCID mice in which tumors are perpetuated or from previous dogs). Rivera, B., et al., *Canine Transmissible Venereal Tumor: A Large-Animal Transplantable Tumor Model*, Comparative Medicine, 2005, 55(4):335-43. These tumors can be treated using the MR visible seeds for the purposes of investigating the ability to use MRI to follow-up treatment with implanted therapy strands. All animal experiments will be conducted under the supervision of and in accordance with The University of Texas M. D. Anderson Cancer Center's Internal Animal Care and Use Committee Guidelines.

All MR procedures can be performed on a clinical 1.5 T scanner (Excite HD, Waukesha, Wis.) which has been used extensively for minimally invasive procedure development in large animal models in the past. McNichols, R. J., et al., *Percutaneous MRI Guided Laser Thermal Therapy in Canine Prostate*, SPIE, 2005, 5686:214; Diederich, C. J., et al., *Transurethral Ultrasound Applicators with Directional Heating Patterns for Prostate Thermal Therapy: In Vivo Evaluation Using Magnetic Resonance Thermometry*, Medical Physics, 2004, 31(2):405-13; Kangasaniemi, M., et al., *Dynamic Gadolinium Uptake in Thermally Treated Canine Brain Tissue and Experimental Cerebral Tumors*, Investigative Radiology, 2003, 38(2):102-07; Kangasniemi, M., et al., *Multiplanar MR Temperature-sensitive Imaging of Cerebral Thermal Treatment Using Interstitial Ultrasound Applicators in a Canine Model*, JMRI, 2002, 16(5):522-31; Hazle, J. D., et al., *MRI-Guided Thermal Therapy of Transplanted Tumors in the Canine Prostate Using a Directional Transurethral Ultrasound Applicator*, JMRI, 2002, 15(4):409-17. Animals will be anesthetized (maintained with 1%-5% isofluorane in the MR suite) and brought into the MR suite for imaging. A 4-channel phased array coil cam be placed for imaging (GEHT, Waukesha, Wis.). An integrated endorectal probe (Model BPX-15, MedRad, Inc., Indianola, Pa.) will be filled with a liquid fluorocarbon material (Fluorinert, 3M Co, St.

Paul, Minn.) in order to provide proper loading and enhance the ability to properly shim the magnetic field.

Figure 8:
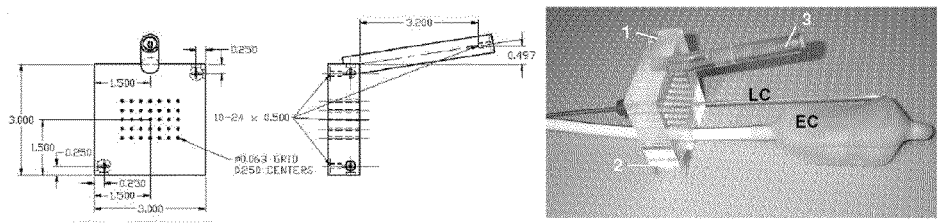
FIG. 8 shows an orthographic projections of the MRI-compatible perineal template for MR-guided prostate treatment delivery.

MRI Protocols: Prior to placement of seeded strands 30, baseline T2-weighted anatomical, diffusion (single-shot fast spin-echo based technique to minimize effects of titanium seeds with b=0, 500), 3D spectroscopic images (PROSE, for non-metal seeds only), high resolution 3D T1-weighted imaging (short echo-time, rf-spoiled gradient-recalled acquisition) and 3D dynamic contrast enhanced (fast rf-spoiled gradient-recalled acquisition technique with Magnevist, 0.2 ml/kg). T2-weighted images (fast spin-echo) can be used to plan the treatment delivery. A 3D fast-recovery fast-spin echo acquisition using parallel imaging will be investigated for providing isotropic resolution T2-weighted images of the prostate anatomy in a reasonable amount of time. If this sequence fails, standard 2D fast spin-echo imaging can be used (e.g., FIG. 3a). Treatment planning images can be performed with a grid template overlay (FIG. 8) adapted to the canine prostate with contrast markers 10 for guiding the placement of radioactive seeds percutaneously (Biotex, Inc, Houston, Tex.) which are registered to the MR coordinate system. McNichols, R. J., et al., *Percutaneous MRI Guided Laser Thermal Therapy in Canine Prostate*, SPIE, 2005, 5686:214.

After seeded strand 30 placement, the prostate can be immediately re-imaged with MRI to evaluate the ability to locate seeds placed in the animal prior to removing the animal from the table. CT imaging can be performed immediately afterward in the Veterinary Research Laboratory. Both MR- and CT-data set images will be fed into the Variseed 7.2 treatment planning system. In order to illustrate the superiority of MR-based dosimetry using contrast markers 10 over CT-based dosimetry, qualitative comparisons between MR- and CT-based dosimetry can be performed on the prostate and critical organ structures. A qualitative comparison of MR-based dosimetry to CT-based dosimetry can be performed. Follow-up MR- and CT-imaging of the animals at 30 and 60 days will facilitate the ability to track the seeds with contrast markers 10 after the prostate edema and intra-prostatic hemorrhage has resolved.

Palladium radioactive therapy seeds 35 where (Pd-103) is selected as a radioactive agent due its relatively short half-life (17 days), clinical applicability, and to permit evaluation of the prostate with functional MR-imaging at 30 and 60 days after approximately 90% of the radiation dose has been delivered. Transmissible venereal tumor (TVT) is introduced into the canine prostate because a reliable tumor model in a large animal that closely resembles the dimensions of humans is not available (Rivera et al. Comparative Medicine 2005). In order to get experimental tumors to grow in the canine prostate, each dog will be immunosuppressed with cyclosporin (10 mg/kg per os b.i.d. for 2 weeks and then s.i.d. until the animal is sacrificed). Immunosuppression therapy commences 7-10 days prior to tumor inoculation.

Figure 9A:
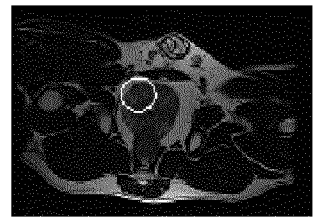
FIG. 9a shows MR localization of TVT tumor (circled) in canine prostate MR T2-weighted.
Figure 9B:
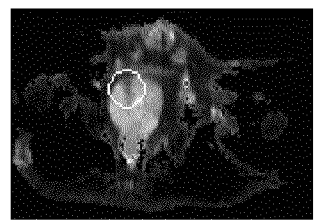
FIG. 9b shows apparent diffusion coefficient maps.
Figure 9C:
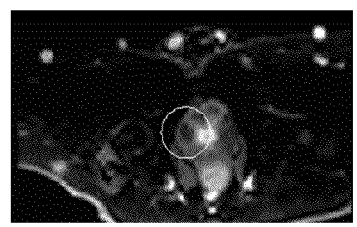
FIG. 9c shows dynamic contrast enhanced imaging with perfusion weighting.
Figure 10A:
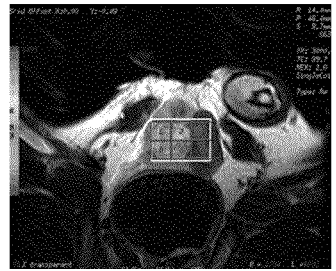
FIG. 10a shows MR spectroscopy of canine TVT in prostate.
Figure 10B:
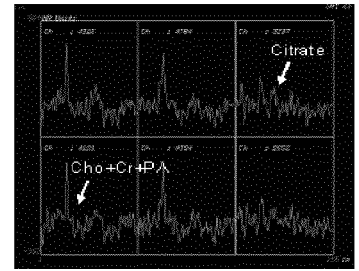
FIG. 10b shows regions of increased choline (Cho) metabolism and decreased citrate metabolism in the region of tumor growth.

For tumor inoculation, dogs will be anesthetized in an operating room dedicated to, and properly equipped for, large animal operating procedures. One lobe of the prostate will be inoculated with TVT (0.25 cc to 0.5 cc) via ventral midline laparotomy access using a 16-20 G needle. Tumors will be allowed to grow for 5-10 weeks to reach maximum diameters of 10-15 mm in the prostate. All animals will be monitored daily for well-being and periodically palpated for tumor development and size. Animals may be periodically (up to weekly) anesthetized and imaged during the tumor growth period to evaluate the tumor growth and size and to obtain baseline MR images prior to therapy seed 35 implantation. MR imaging will utilize an 8-channel phased array coil. Tumor growth will be assessed using MR-diffusion, perfusion and spectroscopic imaging (FIGS. 9-10).

Figure 11A:
FIG. 11a shows gross pathology of a canine prostate.
Figure 11B:
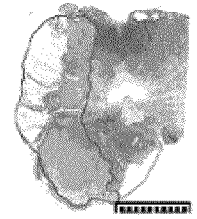
FIG. 11b shows histology stains (H&E) confirming the presence and extent of the TVT and the estimated region of necrosis.
Figure 12:
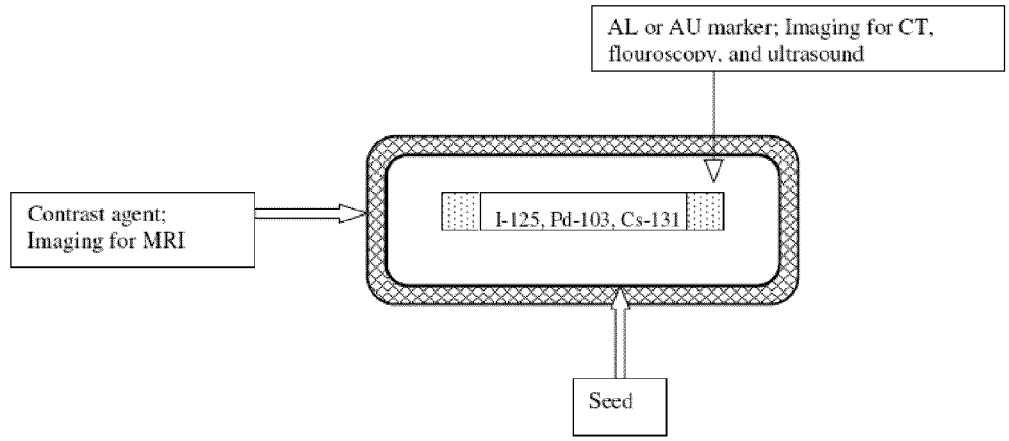
FIG. 12 shows contrast agent mixed or coated with polymer around a radioactive therapy seed.

When the tumor in the prostate is approximately 1.0-1.5 cm, the animal will be prepared for seed placement. Therapy seed 35 placement and imaging will proceed in the MR environment. Baseline MR of the tumor prior to treatment, including diffusion, perfusion, dynamic contrast enhanced imaging (FIG. 9) and spectroscopy (FIG. 10) will be collected and compared to time points at 60 and 90 days post-therapy as illustrated in. Finally, one can correlate the prostate MR functional imaging and pathology (FIG. 11) with MRI-based dosimetry.

The ability to visualize and account for each contrast marker 10 in the seeded strand 30 placed from post-implantation 3D T1-weighted images will be assessed at 60 and 90 days. We will evaluate the ability to manually locate therapy seeds 35 with Variseed 7.2 software and the treatment plan from the 3D T1-weighted images will be assessed. Dose to anatomy and critical organ structures will be determined via a fused T2-weighted anatomical images for manual segmentation.

The effects of non-radioactive seeds (spacer elements 45) on MR imaging quality will be assessed immediately post implantation, and at 60 and 90 days. Anatomical evaluation can be performed to qualitatively assess artifacts and changes in image quality. Following diffusion and dynamic contrast enhanced imaging a qualitative assessment of artifacts and changes in image quality due to the presence of the therapy strand. Quantitative analysis of the apparent diffusion coefficient, DCE initial area under the curve (IAUC) and the total area under the curve (AUC) will be recorded, but it is expected that physiological changes due to the procedure (i.e., inflammation and hemorrhage) may limit the quantitative nature of these results. Following spectroscopy, the effects of the therapy strand will be noted by looking at the relevant calibration parameters (primarily line width after shimming and percent water suppression) for the sequence and the quality of the resulting spectrum (spectral resolution as well as water and lipid suppression over the prostate volume). Results from can be tracked to observe effect of treatment of the prostate.

Figure 4B:
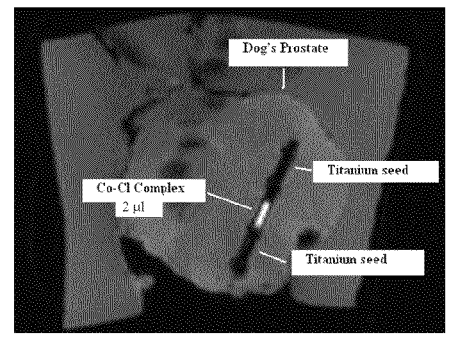
FIG. 4b shows a 1.5-T MRI T1 sagittal image of a dog's prostate with a contrast marker.

Preclinical studies have revealed positive contrast with 0.3-2 micro liters of a solution of contrast agent 20 (FIG. 4b). The small size of the contrast marker 10 with a limited (~0.5 micro liter) amount of contrast agent 20 may require multiple contrast markers 10 for MRI assessments. Geometric distortion can be an impediment to MR treatment planning, but with brachytherapy, this may be minimized do to the proximity of dose to the isocenter. Magnetic susceptibility of metallic therapy seeds 35 may degrade our ability to perform MR spectroscopy. Therefore, a plastic radioactive therapy seed 35 may be more appropriate in this environment.

Ideally, the contrast agent 20 compound is biocompatible and not harmful to the human body. In the *Toxicological Profile for Cobalt* published by the U.S. Department of Health and Human Services in 2004, cobalt is noted to be an essential element for daily consumption and required for Vitamin B12. In the event the capsule of the contrast marker 10 is compromised there should be no cobalt induced toxicity.

This innovative MRI-based approach to prostate brachytherapy with an contrast marker 10 will permit immediate post-operative MRI dosimetric evaluation of the quality of the implant. MRI-based dosimetry can be performed at any center in the country with access to an MRI. If the dose delivered to the prostate cancer is less than adequate, the patient may be taken back to the operating room and additional therapy seeds 35/therapy strand 30 implanted to treat the cancer effectively.

In the future, MRI-guided prostate brachytherapy with a contrast marker 10 would facilitate intraoperative dosimetric evaluation to the prostate cancer and surrounding critical organ structures. Optimizing dose intraoperatively with MRI will ensure that each patient receives the highest quality implant and may result in higher cure rates, decreased side-effects, and an improvement in patients' quality of life.

The contrast marker 10 may permit accurate localization of the radioactive therapy seeds 35 with MRI both during the prostate brachytherapy implant and on subsequent follow-up. Additionally the data obtained by MRI will provide objective analysis to establish national standards of quality for brachytherapy implants. Once the MRI-visible contrast marker 10 is developed, MRI-based prostate brachytherapy dosimetry will be able to accurately define the dose of radiation delivered to the prostate and surrounding critical organ structures. With accurate dose determination, cancer cure rates will increase and side-effects will decrease translating into an improvement in quality of life. The MRI visible contrast marker 10 will permit translatable consistent high-quality prostate brachytherapy implants using MRI-based dosimetry. Therefore, MRI-based prostate brachytherapy dosimetry will immediately replace CT-based dosimetry and permit the establishment of national standards of quality for prostate brachytherapy.

While specific embodiments of the invention have been shown and described in detail to illustrate the application of the principles of the invention, it will be understood that the invention may be embodied otherwise without departing from such principles. For example, these contrast markers can be used for additional applications; stents, drains, filters, balloons for minimally invasive procedures, catheters for both low dose rate (LDR), pulse dose rate (PDR) and high-dose rate (HDR) radiation therapy, applicators for the treatment of gynecologic malignancies, catheters for the treatment of breast and head and neck malignancies, fiducial markers for image guided radiation therapy, MR-guided monitoring probes of thermal therapies (i.e. laser-induced, RF-induced, and cryomediated procedures), biopsy needles, intravascular contrast agent for MRI-guided vascular interventions, guidewires, intraprostatic contrast agent.

What is claimed is:

1. A contrast marker, the marker comprising: a casing; and a contrast agent comprising at least one transition metal complex solution disposed within the casing, wherein the transition metal complex includes $[(CoCl_2)_n(C_2H_5NO_2)_{1-n}]$ (where n=0.5-0.95).

2. The contrast marker of claim 1, further comprising a carrier substrate positioned within the casing.

3. The contrast marker of claim 1, further comprising a radioactive therapeutic agent disposed within the casing.

4. A strand comprising: at least one contrast marker of claim 1 positioned with a strand.

5. The strand of claim 4 further comprising at least one therapy seed wherein the contrast marker and the therapy seed are positioned within the strand.

6. The strand of claim 4 further comprising at least one spacer element.

7. A strand comprising at least one contrast marker of claim 1 and a radioactive agent selected from the group consisting of palladium-103, iodine-125, and cesium-131 wherein said marker and said therapy agent are positioned within a strand.

8. A strand comprising $[(CoCl_2)_n(C_2H_5NO_2)_{1-n}]$ (where n=0.5-0.95), and a therapy seed positioned with a strand.

9. A method of making a strand comprising:
providing a polymer strand having a strand bore;
positioning at least one therapy seed comprising a radioactive agent disposed within a carrier substrate in said strand bore; and
positioning at least one contrast marker in said strand bore in a spaced relationship to said therapy seed, wherein the contrast marker includes $[(CoCl_2)_n(C_2H_5NO_2)_{1-n}]$ (where n=0.5-0.95).

10. The method of claim 9 further comprising positioning a spacer element within the strand bore.

11. A contrast agent comprising $[(CoCl_2)_{n(C_2}H_5NO_2)_{1-n}]$ (where n=0.5-0.95).

12. A therapy seed comprising a radioactive agent wherein said seed further comprises a contrast marker disposed within said seed, wherein the contrast marker includes $[(CoCl_2)_n(C_2H_5NO_2)_{1-n}]$ (where n=0.5-0.95).

13. A therapy seed comprising a radioactive agent wherein said seed further comprises the contrast agent of claim 11.

14. A therapy seed of claim 13 wherein said therapy seed is coated with the contrast agent.

15. A contrast marker, the marker comprising: an casing; and
a contrast agent comprising $[(CoCl_2)_n(C_2H_5NO_2)_{1-n}]$ (where n=0.5-0.95), wherein the agent is coated around the casing.

16. A method of making a contrast agent useful in magnetic resonance imaging comprising the steps of:
determining the T1 relaxation time of a first contrast agent comprising $[(CoCl_2)_n(C_2H_5NO_2)_{1-n}]$ (where n=0.5-0.95); and
providing a second contrast agent wherein the concentration level of the second contrast agent is adjusted so as to produce substantially similar T1 relaxation times for MR imaging to the first contrast agent.

17. The method of claim 16, wherein the second contrast agent is a contrast agent comprising gadolinium chelated with a multidentate ligand.

* * * * *

UNITED STATES PATENT AND TRADEMARK OFFICE
CERTIFICATE OF CORRECTION

PATENT NO. : 8,529,872 B2
APPLICATION NO. : 12/668585
DATED : September 10, 2013
INVENTOR(S) : Steven J. Frank et al.

Page 1 of 1

It is certified that error appears in the above-identified patent and that said Letters Patent is hereby corrected as shown below:

In the Claims:

At Column 40, Line 25, of Claim 11 please capitalize parenthesis and letter "C" in the formula as shown below:

" $[(CoCl_2)_{n}(c_2H_5NO_2)_{1-n}]$ " should be changed to -- $[(CoCl_2)_{n}(C_2H_5NO_2)_{1-n}]$ --

Signed and Sealed this
Eighth Day of October, 2013

Teresa Stanek Rea
*Deputy Director of the United States Patent and Trademark Office*